United States Patent
Gao et al.

(10) Patent No.: US 10,975,391 B2
(45) Date of Patent: Apr. 13, 2021

(54) RECOMBINANT AAV VECTORS USEFUL FOR REDUCING IMMUNITY AGAINST TRANSGENE PRODUCTS

(71) Applicant: University of Massachusetts, Boston, MA (US)

(72) Inventors: Guangping Gao, Westborough, MA (US); Phillip D. Zamore, Northborough, MA (US); Shaoyong Li, Hopkinton, MA (US)

(73) Assignee: University of Massachusetts, Boston, MA (US)

( * ) Notice: Subject to any disclaimer, the term of this patent is extended or adjusted under 35 U.S.C. 154(b) by 240 days.

(21) Appl. No.: 15/306,543

(22) PCT Filed: Apr. 24, 2015

(86) PCT No.: PCT/US2015/027591
§ 371 (c)(1),
(2) Date: Oct. 25, 2016

(87) PCT Pub. No.: WO2015/164786
PCT Pub. Date: Oct. 29, 2015

(65) Prior Publication Data
US 2017/0166925 A1 Jun. 15, 2017
US 2018/0066279 A9 Mar. 8, 2018

Related U.S. Application Data

(60) Provisional application No. 62/001,280, filed on May 21, 2014, provisional application No. 61/984,460, filed on Apr. 25, 2014.

(51) Int. Cl.
| | |
|---|---|
| *C12N 15/86* | (2006.01) |
| *C12N 15/113* | (2010.01) |
| *A61K 31/713* | (2006.01) |
| *C12N 7/00* | (2006.01) |
| *C12N 15/117* | (2010.01) |
| *A61K 38/17* | (2006.01) |
| *A61K 38/28* | (2006.01) |
| *A61K 38/44* | (2006.01) |
| *A61K 38/48* | (2006.01) |
| *A61K 38/51* | (2006.01) |
| *A61K 48/00* | (2006.01) |
| *C07K 16/10* | (2006.01) |
| *C07K 16/22* | (2006.01) |
| *C07K 16/28* | (2006.01) |
| *C07K 16/32* | (2006.01) |

(52) U.S. Cl.
CPC .......... *C12N 15/86* (2013.01); *A61K 38/1709* (2013.01); *A61K 38/28* (2013.01); *A61K 38/446* (2013.01); *A61K 38/4846* (2013.01); *A61K 38/51* (2013.01); *A61K 48/0008* (2013.01); *C07K 16/10* (2013.01); *C07K 16/22* (2013.01); *C07K 16/2875* (2013.01); *C07K 16/2887* (2013.01); *C07K 16/32* (2013.01); *C12N 7/00* (2013.01); *C12N 15/113* (2013.01); *C12N 15/117* (2013.01); *C12N 2310/141* (2013.01); *C12N 2310/17* (2013.01); *C12N 2320/30* (2013.01); *C12N 2330/51* (2013.01); *C12N 2710/10322* (2013.01); *C12N 2710/10332* (2013.01); *C12N 2750/14143* (2013.01); *C12N 2760/00042* (2013.01); *C12N 2830/008* (2013.01); *C12Y 115/01001* (2013.01); *C12Y 304/21022* (2013.01); *C12Y 401/01028* (2013.01)

(58) Field of Classification Search
None
See application file for complete search history.

(56) References Cited

U.S. PATENT DOCUMENTS

| | | |
|---|---|---|
| 5,478,745 A | 12/1995 | Samulski et al. |
| 5,871,982 A | 2/1999 | Wilson et al. |
| 6,251,677 B1 | 6/2001 | Wilson et al. |
| 6,485,966 B2 | 11/2002 | Gao et al. |
| 6,544,786 B1 | 4/2003 | Xiao et al. |
| 6,690,757 B1 * | 2/2004 | Bunton .................. H04L 25/14 370/427 |
| 6,953,690 B1 | 10/2005 | Gao et al. |
| 7,022,519 B2 | 4/2006 | Gao et al. |
| 7,235,393 B2 | 6/2007 | Gao et al. |
| 7,427,396 B2 | 9/2008 | Arbetman et al. |
| 7,456,015 B2 | 11/2008 | Bohn et al. |
| 7,906,111 B2 | 3/2011 | Wilson et al. |
| 8,222,221 B2 | 7/2012 | Corey et al. |
| 8,524,446 B2 | 9/2013 | Gao et al. |

(Continued)

FOREIGN PATENT DOCUMENTS

| | | |
|---|---|---|
| WO | WO 2003/042397 | 5/2003 |
| WO | WO 2005/033321 | 4/2005 |

(Continued)

OTHER PUBLICATIONS

Fumoto et al, Targeted Gene Delivery: Importance of Administration Routes, Chapter 1, Intech, 2013, pp. 3-31.*
Lu and Liton, MicroRNA in the immune system, microRNA as an immune system, Immunology, 2009, pp. 291-298.*
Mao et al, miR-30 Family: A Promising Regulator in Development and Disease, BioMed Research International, 2018, pp. 1-8.*
Wang et al, In Vivo Delivery Systems for Therapeutic Genome Editing, International Journal of Molecular Sciences 17(5):626 ∎ Apr. 2016, pp. 1-19.*
Cox et al, Therapeutic Genome Editing: Prospects and Challenges, Nat Med. Feb. 2015 ; 21(2): 1-26.*

(Continued)

*Primary Examiner* — Maria Marvich
(74) *Attorney, Agent, or Firm* — Wolf, Greenfield & Sacks, P.C.

(57) ABSTRACT

The disclosure in some aspects, relates to nucleic acids, compositions and kits useful for gene therapy with reduced immune response to transgene products.

7 Claims, 22 Drawing Sheets

Specification includes a Sequence Listing.

(56) References Cited

U.S. PATENT DOCUMENTS

| | | | |
|---|---|---|---|
| 8,734,809 B2 | 5/2014 | Gao et al. | |
| 9,102,949 B2 | 8/2015 | Gao et al. | |
| 9,217,155 B2 | 12/2015 | Gao et al. | |
| 9,226,976 B2 | 1/2016 | Flotte et al. | |
| 9,249,424 B2 | 2/2016 | Wolf et al. | |
| 9,272,053 B2 | 3/2016 | Gao et al. | |
| 9,284,357 B2 | 3/2016 | Gao et al. | |
| 9,546,369 B2 | 1/2017 | Gao et al. | |
| 9,596,835 B2 | 3/2017 | Gao et al. | |
| 9,701,984 B2 | 7/2017 | Gao et al. | |
| 9,885,057 B2 | 2/2018 | Flotte et al. | |
| 2001/0016355 A1 | 8/2001 | Samulski et al. | |
| 2002/0164783 A1 | 11/2002 | Feldhaus | |
| 2002/0192823 A1 | 12/2002 | Bartlett | |
| 2003/0103939 A1 | 6/2003 | Engelhardt et al. | |
| 2003/0110526 A1 | 6/2003 | Brown et al. | |
| 2003/0138772 A1 | 7/2003 | Gao et al. | |
| 2004/0101514 A1 | 5/2004 | Liu et al. | |
| 2004/0219528 A1 | 11/2004 | Morris et al. | |
| 2005/0032219 A1 | 2/2005 | Aubourg et al. | |
| 2005/0037988 A1 | 2/2005 | Zamore et al. | |
| 2005/0137153 A1 | 6/2005 | McSwiggen et al. | |
| 2005/0255086 A1 | 11/2005 | Davidson et al. | |
| 2005/0255089 A1 | 11/2005 | Chiorini et al. | |
| 2005/0287122 A1 | 12/2005 | Bartlett et al. | |
| 2006/0063174 A1 | 3/2006 | Turner et al. | |
| 2006/0093589 A1 | 5/2006 | Warrington et al. | |
| 2006/0189564 A1 | 8/2006 | Burright et al. | |
| 2006/0228800 A1 | 10/2006 | Lin et al. | |
| 2006/0292117 A1 | 12/2006 | Loiler et al. | |
| 2007/0036760 A1 | 2/2007 | Wilson et al. | |
| 2007/0243526 A1 | 10/2007 | Kay et al. | |
| 2007/0292410 A1 | 12/2007 | Cashman et al. | |
| 2009/0042828 A1 | 2/2009 | Xu et al. | |
| 2009/0111766 A1 | 4/2009 | Atkinson et al. | |
| 2009/0131355 A1 | 5/2009 | Bot et al. | |
| 2009/0149409 A1 | 6/2009 | Bohn et al. | |
| 2009/0215879 A1 | 8/2009 | DiPrimio et al. | |
| 2010/0041737 A1* | 2/2010 | Naldini | A61P 17/06 514/44 R |
| 2010/0186103 A1* | 7/2010 | Gao | C12N 15/111 800/13 |
| 2010/0323001 A1 | 12/2010 | Pachuk | |
| 2011/0171262 A1 | 7/2011 | Bakker et al. | |
| 2011/0172293 A1 | 7/2011 | Fish et al. | |
| 2011/0212520 A1 | 9/2011 | Davidson et al. | |
| 2011/0258716 A1 | 10/2011 | Baltimore et al. | |
| 2012/0041048 A1* | 2/2012 | Weinberg | C12N 15/113 514/44 A |
| 2012/0137379 A1* | 5/2012 | Gao | C07K 14/005 800/8 |
| 2012/0270930 A1 | 10/2012 | Van Der Maarel et al. | |
| 2012/0309050 A1 | 12/2012 | Kumon et al. | |
| 2013/0030042 A1 | 1/2013 | Couto | |
| 2013/0101558 A1 | 4/2013 | Gao et al. | |
| 2013/0109742 A1 | 5/2013 | Hewitt et al. | |
| 2013/0142861 A1 | 6/2013 | Tsou et al. | |
| 2013/0195801 A1 | 8/2013 | Gao et al. | |
| 2013/0281516 A1 | 10/2013 | Gao et al. | |
| 2014/0142161 A1 | 5/2014 | Flotte et al. | |
| 2014/0142288 A1 | 5/2014 | Davidson et al. | |
| 2014/0147418 A1* | 5/2014 | Chiorini | A61K 38/1774 424/93.6 |
| 2014/0179770 A1 | 6/2014 | Zhang et al. | |
| 2014/0296486 A1 | 10/2014 | Gao et al. | |
| 2014/0335054 A1 | 11/2014 | Gao et al. | |
| 2016/0208257 A1 | 1/2016 | Gao et al. | |
| 2016/0135438 A1 | 5/2016 | Gao et al. | |
| 2016/0186211 A1 | 6/2016 | Flotte et al. | |
| 2016/0222067 A1 | 8/2016 | Gao et al. | |
| 2016/0326524 A1 | 11/2016 | Flotte et al. | |
| 2017/0114340 A1 | 4/2017 | Mueller et al. | |
| 2017/0145439 A1 | 5/2017 | Gao et al. | |
| 2017/0159071 A9 | 6/2017 | Flotte et al. | |
| 2017/0165377 A1 | 6/2017 | Gao et al. | |
| 2017/0166927 A1 | 6/2017 | Gao et al. | |
| 2017/0191039 A1 | 7/2017 | Gao et al. | |
| 2018/0023094 A1 | 1/2018 | Gao et al. | |
| 2018/0037877 A1 | 2/2018 | Gao et al. | |
| 2018/0094264 A1 | 4/2018 | Mueller et al. | |

FOREIGN PATENT DOCUMENTS

| | | |
|---|---|---|
| WO | WO 2006/031267 A2 | 3/2006 |
| WO | WO 2006/066066 A2 | 6/2006 |
| WO | WO 2006/119432 A2 | 11/2006 |
| WO | WO 2007/000668 A2 | 1/2007 |
| WO | WO 2007/027775 A2 | 3/2007 |
| WO | WO 2008/091703 | 7/2008 |
| WO | WO 2008/125846 A2 | 10/2008 |
| WO | WO 2008/147839 A1 | 12/2008 |
| WO | WO 2008/150897 A2 | 12/2008 |
| WO | WO 2009/079592 A2 | 6/2009 |
| WO | WO 2009/109665 A1 | 9/2009 |
| WO | WO 2009/146178 A1 | 12/2009 |
| WO | WO 2010/027446 A2 | 3/2010 |
| WO | WO 2010/034314 A1 | 4/2010 |
| WO | WO 2010/071454 A1 | 6/2010 |
| WO | WO 2010/099383 A2 | 9/2010 |
| WO | WO 2010/129021 A1 | 11/2010 |
| WO | WO 2010/138263 A2 | 12/2010 |
| WO | WO 2011/094198 A1 | 8/2011 |
| WO | WO 2011/133890 A1 | 10/2011 |
| WO | WO 2013/055865 A1 | 4/2013 |
| WO | WO 2013/123503 A1 | 8/2013 |
| WO | WO 2013/170078 A1 | 11/2013 |
| WO | WO 2013/190059 A1 | 12/2013 |
| WO | WO 2014/160092 A1 | 10/2014 |
| WO | WO 2014/186746 A1 | 11/2014 |
| WO | WO 2014/197748 A2 | 11/2014 |
| WO | WO 2015/121501 A1 | 8/2015 |
| WO | WO 2015/168666 A2 | 11/2015 |
| WO | WO 2016/065001 A1 | 4/2016 |
| WO | WO 2017/023724 A1 | 2/2017 |

OTHER PUBLICATIONS

Aartsma-Rus et al., New insights in gene-derived therapy: the example of Duchenne muscular dystrophy. Ann N Y Acad Sci. Dec. 2010;1214:199-212. doi: 10.1111/j.1749-6632.2010.05836.x. Epub Dec. 1, 2010.

Adachi et al., Drawing a high-resolution functional map of adeno-associated virus capsid by massively parallel sequencing. Nat Commun. 2014;5:3075. doi: 10.1038/ncomms4075.

Alisky et al., Gene therapy for amyotrophic lateral sclerosis and other motor neuron diseases. Hum Gene Ther. Nov. 20, 2000;11(17):2315-29.

Arbuthnot et al., Hepatic delivery of RNA interference activators for therapeutic application. Curr Gene Ther. Apr. 2009;9(2):91-103.

Asokan et al., The AAV vector toolkit: poised at the clinical crossroads. Mol Ther. Apr. 2012;20(4):699-708. doi: 10.1038/mt.2011.287. Epub Jan. 24, 2012.

Azzouz et al., VEGF delivery with retrogradely transported lentivector prolongs survival in a mouse ALS model. Nature. May 27, 2004;429(6990):413-7.

Baek et al., AAV-mediated gene delivery in adult GM1-gangliosidosis mice corrects lysosomal storage in CNS and improves survival. PLoS One. Oct. 18, 2010;5(10):e13468. doi: 10.1371/journal.pone.0013468.

Berns et al., Biology of adeno-associated virus. Curr Top Microbiol Immunol. 1996;218:1-23.

Beutler et al., AAV for pain: steps towards clinical translation. Gene Ther. Apr. 2009;16(4):461-9. Epub Mar. 5, 2009.

Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.

Brown et al., A microRNA-regulated lentiviral vector mediates stable correction of hemophilia B mice. Blood. Dec. 15, 2007;110(13):4144-52. Epub Aug. 28, 2007.

(56) References Cited

OTHER PUBLICATIONS

Brown et al., Endogenous microRNA can be broadly exploited to regulate transgene expression according to tissue, lineage and differentiation state. Nat Biotechnol. Dec. 2007;25(12):1457-67. Epub Nov. 16, 2007.

Brown et al., Endogenous microRNA regulation suppresses transgene expression in hematopoietic lineages and enables stable gene transfer. Nat Med. May 2006;12(5):585-91. Epub Apr. 23, 2006.

Buning et al., Receptor targeting of adeno-associated virus vectors. Gene Ther. Jul. 2003;10(14):1142-51.

Büssing et al., let-7 microRNAs in development, stem cells and cancer. Trends Mol Med. Sep. 2008;14(9):400-9. doi: 10.1016/j.molmed.2008.07.001. Epub Jul. 31, 2008.

Calcedo et al., Worldwide epidemiology of neutralizing antibodies to adeno-associated viruses. J Infect Dis. Feb. 1, 2009;199(3):381-90.

Carter et al., Adeno-associated virus gene expression and regulation. CRC Handbook of parvoviruses. 1990:227-54.

Carter, in "Handbook of Parvoviruses", ed., P. Tijsser, CRC Press, pp. 155-168 (1990).

Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.

Chadderton et al., Improved retinal function in a mouse model of dominant retinitis pigmentosa following AAV-delivered gene therapy. Mol Ther. Apr. 2009;17(4):593-9. Epub Jan. 27, 2009.

Chang et al., miR-122, a mammalian liver-specific microRNA, is processed from her mRNA and may downregulate the high affinity cationic amino acid transporter CAT-1. RNA Biol. Jul. 2004;1(2):106-13. Epub Jul. 1, 2004.

Chen et al., Efficient transduction of vascular endothelial cells with recombinant adeno-associated virus serotype 1 and 5 vectors. Hum Gene Ther. Feb. 2005;16(2):235-47.

Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.

Chen et al., Regulation of immune responses and tolerance: the microRNA perspective. Immunol Rev. May. 2013;253(1):112-28. doi:10.1111/imr.12060.

Cheng et al., Development of optimized AAV3 serotype vectors: mechanism of high-efficiency transduction of human liver cancer cells. Gene Ther. Apr. 2012;19(4):375-84. doi: 10.1038/gt.2011.105. Epub Jul. 21, 2011.

Chiorini et al., Cloning and characterization of adeno-associated virus type 5. J Virol. Feb. 1999;73(2):1309-19.

Choudhury et al., Identification of Novel vectors capable of CNS transduction in adult mice after single round selection using DNA shuffled AAV capsid library. Mol Ther. May 1, 2013;21(1):S1.

Christensen et al., A let-7 microRNA-binding site polymorphism in the KRAS 3' UTR is associated with reduced survival in oral cancers. Carcinogenesis. Jun. 2009;30(6):1003-7. doi: 10.1093/carcin/bgp099. Epub Apr. 20, 2009.

Conlon et al., Efficient hepatic delivery and expression from a recombinant adeno-associated virus 8 pseudotyped alpha1-antitrypsin vector. Mol Ther. Nov. 2005;12(5):867-75. Epub Aug. 8, 2005.

Coulouarn et al., Loss of miR-122 expression in liver cancer correlates with suppression of the hepatic phenotype and gain of metastatic properties. Oncogene. Oct. 8, 2009;28(40):3526-36. doi: 10.1038/onc.2009.211. Epub Jul. 20, 2009.

Csak et al., microRNA-122 regulates hypoxia-inducible factor-1 and vimentin in hepatocytes and correlates with fibrosis in diet-induced steatohepatitis. Liver Int. Feb. 2015;35(2):532-41. doi: 10.1111/liv.12633. Epub Jul. 28, 2014.

Czech, MicroRNAs as therapeutic targets. N Engl J Med. Mar. 16, 2006;354(11):1194-5.

Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.

Davidson et al., Recombinant adeno-associated virus type 2, 4, and 5 vectors: transduction of variant cell types and regions in the mammalian central nervous system. Proc Natl Acad Sci U S A. Mar. 28, 2000;97(7):3428-32.

Daya et al., Gene therapy using adeno-associated virus vectors. Clin Microbiol Rev. Oct. 2008;21(4):583-93. doi: 10.1128/CMR.00008-08.

Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.

Eberling et al., Results from a phase I safety trial of hAADC gene therapy for Parkinson disease. Neurology. May 20, 2008;70(21):1980-3. doi: 10.1212/01.wnl.0000312381.29287.ff. Epub Apr. 9, 2008.

Ebert et al., MicroRNA sponges: competitive inhibitors of small RNAs in mammalian cells. Nat Methods. Sep. 2007;4(9):721-6. Epub Aug. 12, 2007.

Elmén et al., LNA-mediated microRNA silencing in non-human primates. Nature. Apr. 2008;452(17): 896-900.

Elmén et al., Antagonism of microRNA-122 in mice by systemically administered LNA-antimiR leads to up-regulation of a large set of predicted target mRNAs in the liver. Nucleic Acids Res. Mar. 2008;36(4):1153-62. Epub Dec. 23, 2007.

Esau et al., miR-122 regulation of lipid metabolism revealed by in vivo antisense targeting. Cell Metab. Feb. 2006;3(2):87-98.

Fabani et al., miR-122 targeting with LNA/2'-O-methyl oligonucleotide mixmers, peptide nucleic acids (PNA), and PNA-peptide conjugates. RNA. Feb. 2008;14(2):336-46. Epub Dec. 11, 2007.

Fechner et al., Cardiac-targeted RNA interference mediated by an AAV9 vector improves cardiac function in coxsackievirus B3 cardiomyopathy. J Mol Med (Berl). Sep. 2008;86(9):987-97. doi: 10.1007/s00109-008-0363-x. Epub Jun. 12, 2008.

Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.

Fisher et al., Transduction with recombinant adeno-associated virus for gene therapy is limited by leading-strand synthesis. J Virol. Jan. 1996;70(1):520-32.

Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.

Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.

Forman et al., A search for conserved sequences in coding regions reveals that the let-7 microRNA targets Dicer within its coding sequence. Proc Natl Acad Sci U S A. Sep. 30, 2008;105(39):14879-84. doi: 10.1073/pnas.0803230105. Epub Sep. 23, 2008.

Foust et al., Intravascular AAV9 preferentially targets neonatal-neurons and adult-astrocytes. Nature Biotechnology, 27; 59-65 2009.

Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.

Gadalla et al., Improved survival and reduced phenotypic severity following AAV9/MECP2 gene transfer to neonatal and juvenile male Mecp2 knockout mice. Mol Ther. Jan. 2013;21(1):18-30. doi:10.1038/mt.2012.200. Epub Sep. 25, 2012.

Gao et al., Inadvertent gene transfer of co-packaged rep and cap sequences during the production of AAV vector and its potential impact on vector performance. Molecular Therapy. May 2008;16(Suppl. 1):S105-S106. Abstract 279.

Gao et al., Novel adeno-associated viruses from rhesus monkeys as vectors for human gene therapy. Proc Natl Acad Sci U S A. Sep. 3, 2002;99(18):11854-9. Epub Aug. 21, 2002.

Gao et al., RAAV-mediated targeting in adult mice and its potential in generating animal models of tissue-specific somatic transgenics or knock down. Molecular Therapy. May 2008;16(1):S118-S119. Abstract 316.

(56) References Cited

OTHER PUBLICATIONS

Gentner et al., Stable knockdown of microRNA in vivo by lentiviral vectors. Nat Methods. Jan. 2009;6(1):63-6. doi: 10.1038/nmeth. 1277. Epub Nov. 30, 2008.
Girard et al., miR-122, a paradigm for the role of microRNAs in the liver. J Hepatol. Apr. 2008;48(4):648-56. doi: 10.1016/j.jhep.2008. 01.019. Epub Feb. 12, 2008.
Gramantieri et al., Cyclin G1 is a target of miR-122a, a microRNA frequently down-regulated in human hepatocellular carcinoma. Cancer Res. Jul. 1, 2007;67(13):6092-9.
Grimm et al., Fatality in mice due to oversaturation of cellular microRNA/short hairpin RNA pathways. Nature. May 25, 2006;441(7092):537-41.
Grimm, Small silencing RNAs: state-of-the-art. Adv Drug Deliv Rev. Jul. 25, 2009;61(9):672-703. doi: 10.1016/j.addr.2009.05.002. Epub May 7, 2009.
Haraguchi et al., Vectors expressing efficient RNA decoys achieve the long-term suppression of specific microRNA activity in mammalian cells. Nucleic Acids Res. Apr. 2009;37(6):e43. doi: 10.1093/nar/gkp040. Epub Feb. 17, 2009.
Haussecker et al., miR-122 continues to blaze the trail for microRNA therapeutics. Mol Ther. Feb. 2010;18(2):240-2. doi: 10.1038/mt. 2009.313.
Hildinger et al., Hybrid vectors based on adeno-associated virus serotypes 2 and 5 for muscle-directed gene transfer. J Virol. Jul. 2001;75(13):6199-203.
Horwich et al., Design and delivery of antisense oligonucleotides to block microRNA function in cultured *Drosophila* and human cells. Nat Protoc. 2008;3(10):1537-49. doi: 10.1038/nprot.2008.145.
Hsu et al., Essential metabolic, anti-inflammatory, and anti-tumorigenic functions of miR-122 in liver. J Clin Invest. Aug. 2012;122(8):2871-83. doi:10.1172/JCI63539. Epub Jul. 23, 2012.
Hutvágner et al., Sequence-specific inhibition of small RNA function. PLoS Biol. Apr. 2004;2(4):E98. Epub Feb. 24, 2004.
Iida et al., Systemic Delivery of Tyrosine-Mutant AAV Vectors Results in Robust Transduction of Neurons in Adult Mice. BioMed Res Int. 2013;2013.
Jakobsson et al., Lentiviral vectors for use in the central nervous system. Mol Ther. Mar. 2006;13(3):484-93. Epub Jan. 3, 2006.
Johnson et al., RAS is regulated by the let-7 microRNA family. Cell. Mar. 11, 2005;120(5):635-47.
Kaspar et al., Retrograde viral delivery of IGF-1 prolongs survival in a mouse ALS model. Science. Aug. 8, 2003;301(5634):839-42.
Kota et al., AAV8-Mediated Delivery of miR-26a inhibits cancer cell proliferation and induces tumor-specific apoptosis in a liver cancer model. Mol. Therapy. May 2009. 17(1):S300. Abstract 783.
Kota et al., Therapeutic microRNA delivery suppresses tumorigenesis in a murine liver cancer model. Cell. Jun. 12, 2009;137(6):1005-17. doi: 10.1016/j.cell.2009.04.021.
Kotin et al., Organization of adeno-associated virus DNA in latently infected Detroit 6 cells. Virology. Jun. 1989;170(2):460-7.
Kotin et al., Site-specific integration by adeno-associated virus. Proc Natl Acad Sci U S A. Mar. 1990;87(6):2211-5.
Krützfeldt et al., Silencing of microRNAs in vivo with 'antagomirs'. Nature. Dec. 1, 2005;438(7068):685-9. Epub Oct. 30, 2005.
Kutay et al., Downregulation of miR-122 in the rodent and human hepatocellular carcinomas. J Cell Biochem. Oct. 15, 2006;99(3):671-8.
Lanford et al., Therapeutic silencing of microRNA-122 in primates with chronic hepatitis C virus infection. Science. Jan. 8, 2010;327(5962):198-201. Epub Dec. 3, 2009.
Lawlor et al., Efficient gene delivery and selective transduction of glial cells in the mammalian brain by AAV serotypes isolated from nonhuman primates. Mol Ther. Oct. 2009;17(10):1692-702. doi:10. 1038/mt.2009.170.
Levitskaya et al., Inhibition of antigen processing by the internal repeat region of the Epstein-Barr virus nuclear antigen-1. Nature. Jun. 22, 1995;375(6533):685-8.

Lewis et al., Conserved seed pairing, often flanked by adenosines, indicates that thousands of human genes are microRNA targets. Cell. Jan. 14, 2005;120(1):15-20.
Lewis et al., Prediction of mammalian microRNA targets. Cell. Dec. 26, 2003;115(7):787-98.
Li et al., Efficient and Targeted Transduction of Nonhuman Primate Liver With Systemically Delivered Optimized AAV3B Vectors. Mol Ther. Dec. 2015;23(12):1867-76. doi: 10.1038/mt.2015.174. Epub Sep. 25, 2015.
Li et al., Intronic microRNA: discovery and biological implications. DNA Cell Biol. Apr. 2007;26(4):195-207.
Li et al., Protein trans-splicing as a means for viral vector-mediated in vivo gene therapy. Hum Gene Ther. Sep. 2008;19(9):958-64. doi: 10.1089/hum.2008.009.
Lowenstein, Crossing the rubicon. Nat Biotechnol. Jan. 2009;27(1):42-4.
Loya et al., Transgenic microRNA inhibition with spatiotemporal specificity in intact organisms. Nat Methods. Dec. 2009;6(12):897-903. doi: 10.1038/nmeth.1402. Epub Nov. 15, 2009.
Lux et al., Green fluorescent protein-tagged adeno-associated virus particles allow the study of cytosolic and nuclear trafficking. J Virol. Sep. 2005;79(18):11776-87.
Lynn, Meta-regulation: microRNA regulation of glucose and lipid metabolism. Trends Endocrinol Metab. Nov. 2009;20(9):452-9. doi: 10.1016/j.tem.2009.05.007. Epub Sep. 30, 2009.
Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.
Maguire et al., Gene therapy for the nervous system: challenges and new strategies. Neurotherapeutics. Oct. 2014;11(4):817-39. doi: 10.1007/s13311-014-0299-5.
Mandel et al., Recombinant adeno-associated viral vectors as therapeutic agents to treat neurological disorders. Mol Ther. Mar. 2006;13(3):463-83. Epub Jan. 18, 2006.
Matalon et al., Adeno-associated virus-mediated aspartoacylase gene transfer to the brain of knockout mouse for canavan disease. Mol Ther. May 2003;7(5 Pt 1):580-7.
McBride et al., Artificial miRNAs mitigate shRNA-mediated toxicity in the brain: implications for the therapeutic development of RNAi. Proc Natl Acad Sci U S A. Apr. 15, 2008;105(15):5868-73. Epub Apr. 8, 2008.
McCarty et al., Adeno-associated virus terminal repeat (TR) mutant generates self-complementary vectors to overcome the rate-limiting step to transduction in vivo. Gene Ther. Dec. 2003;10(26):2112-8.
McCarty et al., Integration of adeno-associated virus (AAV) and recombinant AAV vectors. Annu Rev Genet. 2004;38:819-45.
McCarty et al., Self-complementary recombinant adeno-associated virus (scAAV) vectors promote efficient transduction independently of DNA synthesis. Gene Ther. Aug. 2001;8(16):1248-54.
McCarty, Self-complementary AAV vectors; advances and applications. Mol Ther. Oct. 2008;16(10):1648-56. Epub Aug. 5, 2008.
McCurdy et al., Sustained normalization of neurological disease after intracranial gene therapy in a feline model. Sci Transl Med. Apr. 9, 2014;6(231):231ra48. doi: 10.1126/scitranslmed.3007733.
Meister et al., Sequence-specific inhibition of microRNA- and siRNA-induced RNA silencing. RNA. Mar. 2004;10(3):544-50.
Mueller et al., Development of Simultaneous Gene Augmentation and Reduction of Mutant Gene Expression with a Single Recombinant AAV for Alpha-1 Antitrypsin Disease. Molecular Therapy May 2009;17(1):S391-S392. Abstract 1030.
Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.
Mueller et al., Using rAAV Delivered miRNAs to Knockdown Misfolded Human Alpha 1 Antitrypsin in a Transgenic Mouse Model. Molecular Therapy May 2010;18(1):S21. Abstract 51.
O'Reilly et al., RNA interference-mediated suppression and replacement of human rhodopsin in vivo. Am J Hum Genet. Jul. 2007;81(1):127-35. Epub May 23, 2007.

(56) References Cited

OTHER PUBLICATIONS

Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.
Pertin et al., Efficacy and specificity of recombinant adeno-associated virus serotype 6 mediated gene transfer to drg neurons through different routes of delivery. Poster sessions. Eur J. Pain. 2009;13:S74. Abstract 229.
Ralph et al., Silencing mutant SOD1 using RNAi protects against neurodegeneration and extends survival in an ALS model. Nat Med. Apr. 2005;11(4):429-33. Epub Mar. 13, 2005.
Raoul et al., Lentiviral-mediated silencing of SOD1 through RNA interference retards disease onset and progression in a mouse model of ALS. Nat Med. Apr. 2005;11(4):423-8. Epub Mar. 13, 2005.
Schnepp et al., Characterization of adeno-associated virus genomes isolated from human tissues. J Virol. Dec. 2005;79(23):14793-803.
Sen et al., Micromanaging vascular biology: tiny microRNAs play big band. J Vasc Res. 2009;46(6):527-40. doi: 10.1159/000226221. Epub Jun. 30, 2009.
Sharipo et al., cis-Inhibition of proteasomal degradation by viral repeats: impact of length and amino acid composition. FEBS Lett. Jun. 15, 2001;499(1-2):137-42.
Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.
Stoica et al., Targeting Human SOD1 Using AAV mediated RNAi in a mouse model of amyotrophic lateral sclerosis. Mol ther. Jun. 2013;21(1):S149.
Storkebaum et al., Treatment of motoneuron degeneration by intracerebroventricular delivery of VEGF in a rat model of ALS. Nat Neurosci. Jan. 2005;8(1):85-92. Epub Nov. 28, 2004.
Tanimizu et al., Downregulation of miR122 by grainyhead-like 2 restricts the hepatocytic differentiation potential of adult liver progenitor cells. Development. Dec. 2014;141(23):4448-56. doi:10.1242/dev.113654. Epub Nov. 18, 2014.
Tenenbaum et al., Recombinant AAV-mediated gene delivery to the central nervous system. J Gene Med. Feb. 2004;6 Suppl 1:S212-22.
Tokumaru et al., let-7 regulates Dicer expression and constitutes a negative feedback loop. Carcinogenesis. Nov. 2008;29(11):2073-7. doi: 10.1093/carcin/bgn187. Epub Aug. 11, 2008.
Tomar et al., Use of adeno-associated viral vector for delivery of small interfering RNA. Oncogene. Aug. 28, 2003;22(36):5712-5.
Towne et al., Systemic AAV6 delivery mediating RNA interference against SOD1: neuromuscular transduction does not alter disease progression in fALS mice. Mol Ther. Jun. 2008;16(6):1018-25. doi:10.1038/mt.2008.73. Epub Apr. 15, 2008.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
Tsai et al., MicroRNA-122, a tumor suppressor microRNA that regulates intrahepatic metastasis of hepatocellular carcinoma. Hepatology. May 2009;49(5):1571-82. doi: 10.1002/hep.22806.
Vandenberghe et al., Heparin binding directs activation of T cells against adeno-associated virus serotype 2 capsid. Nat Med. Aug. 2006;12(8):967-71. Epub Jul. 16, 2006.
Vandenberghe et al., Tailoring the AAV vector capsid for gene therapy. Gene Ther. Mar. 2009;16(3):311-9. Epub Dec. 4, 2008.
Vandendriessche et al., Efficacy and safety of adeno-associated viral vectors based on serotype 8 and 9 vs. lentiviral vectors for hemophilia B gene therapy. J Thromb Haemost. Jan. 2007;5(1):16-24. Epub Sep. 26, 2006.
Vaucheret et al., The action of ARGONAUTE1 in the miRNA pathway and its regulation by the miRNA pathway are crucial for plant development. Genes Dev. May 15, 2004;18(10):1187-97. Epub May 6, 2004.
Vermeulen et al., Double-stranded regions are essential design components of potent inhibitors of RISC function. RNA. May 2007;13(5):723-30. Epub Mar. 30, 2007.
Waldman et al., Applications of microRNA in cancer: Exploring the advantages of miRNA. Clin Transl Sci. Jun. 2009;2(3):248-9. doi: 10.1111/j.1752-8062.2009.00110.x.
Wang et al., Neuroprotective effects of glial cell line-derived neurotrophic factor mediated by an adeno-associated virus vector in a transgenic animal model of amyotrophic lateral sclerosis. J Neurosci. Aug. 15, 2002;22(16):6920-8.
Wang et al., Rescue and replication of adeno-associated virus type 2 as well as vector DNA sequences from recombinant plasmids containing deletions in the viral inverted terminal repeats: selective encapsidation of viral genomes in progeny virions. J Virol. Mar. 1996;70(3):1668-77.
Wang et al., Somatically Repairing Compound Heterozygous Recessive Mutations by Chromosomal Cut-and-Paste for in Vivo Gene Therapy. May 2016. 24(1):S289. Abstract 733.
Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.
Wang et al., The design of vectors for RNAi delivery system. Curr Pharm Des. 2008;14(13):1327-40.
Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.
Wang et al., Therapeutic gene silencing delivered by a chemically modified small interfering RNA against mutant SOD1 slows amyotrophic lateral sclerosis progression. J Biol Chem. Jun. 6, 2008;283(23):15845-52. doi: 10.1074/jbc.M800834200. Epub Mar. 26, 2008.
Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.
Watson et al., Intrathecal administration of AAV vectors for the treatment of lysosomal storage in the brains of MPS I mice. Gene Ther. Jun. 2006;13(11):917-25.
Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.
Weismann, Approaches and Considerations Towards a Safe and Effective Adena-Associated Virus Mediated Therapeutic Intervention for GM 1-Gangliosidosis: A Dissertation. University Massachusetts Medical School. Aug. 5, 2014.
Xia et al., Allele-specific RNAi selectively silences mutant SOD1 and achieves significant therapeutic benefit in vivo. Neurobiol Dis. Sep. 2006;23(3):578-86. Epub Jul. 20, 2006.
Xie et al., Characterization of positioning effect of pol III-shRNA transcription unit in scAAV vector genome on the packaging efficiency and functionality of shRNA silencing. Molecular Therapy. May 2010;18(1): S262. Abstract 671.
Xie et al., MicroRNA regulated tissue specific transduction by rAAV vector. Molecular Therapy. May 2009;17(1): S279. Abstract 732.
Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.
Xie et al., rAAV-mediated delivery of micro RNA scavengers leads to efficient and stable knock-down of cognate micro RNAs, upregulation of their natural target genes and phenotypic changes in mice. Molecular Therapy. May 2010;18(1): S140. Abstract 362.
Xu et al., Delivery of MDR1 small interfering RNA by self-complementary recombinant adeno-associated virus vector. Mol Ther. Apr. 2005;11(4):523-30.
Yamanaka et al., Astrocytes as determinants of disease progression in inherited amyotrophic lateral sclerosis. Nat Neurosci. Mar. 2008;11(3):251-3. doi: 10.1038/nn2047. Epub Feb. 3, 2008.
Yan et al., Unique biologic properties of recombinant AAV1 transduction in polarized human airway epithelia. J Biol Chem. Oct. 6, 2006;281(40):29684-92. Epub Aug. 9, 2006.

(56) References Cited

OTHER PUBLICATIONS

Yang et al., The muscle-specific microRNA miR-1 regulates cardiac arrhythmogenic potential by targeting GJA1 and KCNJ2. Nat Med. Apr. 2007;13(4):486-91. Epub Apr. 1, 2007. Erratum in: Nat Med. Dec. 2011;17(12):1693.

Yu et al., let-7 regulates self renewal and tumorigenicity of breast cancer cells. Cell. Dec. 14, 2007;131(6):1109-23.

Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.

Zolotukhin et al., Production and purification of serotype 1, 2, and 5 recombinant adeno-associated viral vectors. Methods. Oct. 2002;28(2):158-67.

Borel et al., Recombinant AAV as a platform for translating the therapeutic potential of RNA interference. Mol Ther. Apr. 2014;22(4):692-701. doi:10.1038/mt.2013.285. Epub Dec. 19, 2013.

Koornneef et al., Apolipoprotein B knockdown by AAV-delivered shRNA lowers plasma cholesterol in mice. Mol Ther. Apr. 2011;19(4):731-40. doi:10.1038/mt.2011.6. Epub Feb. 8, 2011.

Malinkevich et al., 1002. rAAV Mediated Delivery of Target Specific Micro RNA Sponges for Study of Micro RNA Function in Mouse Models. Gene regulation. May 1, 2009;17(1):S382.

Pfeifer et al., Pharmacological potential of RNAi—focus on miRNA. Pharmacol Ther. Jun. 2010;126(3):217-27. doi: 10.1016/j.pharmthera.2010.03.006. Epub Apr. 11, 2010.

Suckau et al., 851. The Effect of Genome Size and Design of scAAV Vectors on Efficiency of shRNA Expression and Gene Knockdown. May 1, 2007;15(1):S325.

Xie et al., 676. DNA Sequences Encoding shRNAs Can Replace Mutant ITR in scAAV Genome for Efficient Replication and Packaging and Transcribe shRNAs by pol III Promoter Activity of wt ITR for Efficient Gene Silencing Mol Therapy. May 2015;23(1):S269.

Xie et al., Short DNA Hairpins Compromise Recombinant Adeno-Associated Virus Genome Homogeneity. Mol Ther. Jun. 7, 2017;25(6):1363-1374. doi: 10.1016/j.ymthe.2017.03.028. Epub Apr. 24, 2017.

* cited by examiner

_US 10,975,391 B2_

RECOMBINANT AAV VECTORS USEFUL FOR REDUCING IMMUNITY AGAINST TRANSGENE PRODUCTS

RELATED APPLICATIONS

This application is a National Stage Application of PCT/US2015/027591, filed Apr. 24, 2015, and entitled "Recombinant AAV Vectors Useful For Reducing Immunity Against Transgene Products", which claims the benefit under 35 U.S.C. § 119 (e) of U.S. provisional applications U.S. Ser. No. 61/984,460, filed Apr. 25, 2014, and entitled "Recombinant AAV Vectors Useful For Reducing Immunity Against Transgene Products", and 62/001,280, filed May 21, 2014, and entitled "Recombinant AAV Vectors Useful For Reducing Immunity Against Transgene Products", the entire contents of each of which are incorporated herein by reference.

FEDERALLY SPONSORED RESEARCH

This invention was made with government support under AI100263 and GM065236 awarded by the National Institutes of Health. The government has certain rights in the invention.

BACKGROUND

Gene therapy is an approach for delivering therapeutic genes to treat human diseases. Adeno-associated viral (AAV) vector is one of the most promising gene transfer vehicles for different therapeutic applications. AAVs can deliver and express genes in a wide variety of tissue and cell types. Additional evidence has demonstrated that these AAVs can mediate persistent, long term expression of the transgenes in animals. Recently, clinical trials using AAV have shown beneficial effects and few side effects in human. However, improved methods of AAV based gene therapy are needed.

SUMMARY

Aspects of the disclosure relate to a recognition that therapeutic gene delivery may lead to inadvertent auto-immunity to endogenous and transgene derived products. For example, a B cell response to a transgene product may result in inhibitory antibodies against the transgene, thereby impairing the treatment. Aspects of the disclosure also relate to a recognition that immunotoxicity may result from inadvertent transduction of antigen presenting cells (APCs), such as dendritic cells, macrophages, and B-lymphocytes. This inadvertent transduction may trigger host immunity towards transgene products. Dendritic cells (DCs) have a broad range of antigen presentation and may represent a key APC in the host. Virally transduced DCs can directly display peptide epitopes on MHC class I molecules after cellular processing. The mature DCs display peptide antigens through MHC class I molecule activated cytotoxic CD8+ T lymphocytes (CTLs). Therefore, aspects of the disclosure, provided methods for reducing transgene expression in APCs, such as DCs. In some embodiments, methods are provided that avoid transgene related immune responses in viral transduction, for example, using recombinant Adeno-Associated Viruses (rAAVs).

Accordingly, the disclosure in some aspects relates to rAAVs, nucleic acids, compositions, kits and related methods useful for performing gene therapy in a manner that reduces the likelihood that an undesirable immune response will occur against therapeutic transgene products. For example, aspects of the disclosure relate to methods of delivering a transgene to target cells of a subject in a manner that minimizes immune responses in the subject against a product of the transgene. In some embodiments, the methods involve administering to the subject a rAAV comprising a transgene engineered to express an RNA transcript that comprises a binding site of at least one immune-associated miRNA, in which the rAAV infects target cells of the subject thereby delivering the transgene to the target cells. In some embodiments, presence of the binding site of the at least one immune-associated miRNA results in a lower immune response in the subject against a product of the RNA transcript compared with the level of an immune response in a control subject. In some embodiments, the control subject is a subject that has been administered a control rAAV comprising a transgene engineered to express a control RNA transcript encoding the product, in which the control RNA transcript does not comprise immune-associated miRNA binding sites. In some embodiments, the RNA transcript comprises binding sites for at least two immune-associated miRNAs. In some embodiments, the RNA transcript comprises binding sites for two to ten different immune-associated miRNAs. In some embodiments, the at least two immune-associated miRNAs are selected from the group consisting of: miR-15a, miR-16-1, miR-17, miR-18a, miR-19a, miR-20a, miR-19b-1, miR-21, miR-29a, miR-29b, miR-29c, miR-30b, miR-31, miR-34a, miR-92a-1, miR-106a, miR-125a, miR-125b, miR-126, miR-142-3p, miR-146a, miR-150, miR-155, miR-181a, miR-223 and miR-424. In some embodiments, the at least two immune-associated miRNAs comprise an miRNA pair recited in a row of Table 1.

According to some aspects of the disclosure, methods are provided of delivering a transgene to target cells of a subject, in which the methods involve administering to the subject a recombinant Adeno-Associated Virus (rAAV) comprising a transgene engineered to express a recombinant protein that comprises Glycine-Alanine repeats. In some embodiments, the Glycine-Alanine repeats inhibit proteasomal processing of the recombinant protein in cells, thereby inhibiting presentation of antigens of the recombinant protein by MHC class I molecules. In some embodiments, the Glycine-Alanine repeats result in a lower immune response in the subject against the recombinant protein compared with the level of an immune response in a control subject that has been administered a control rAAV comprising a transgene engineered to express a control protein that does not comprise the Glycine-Alanine repeats. In some embodiments, other than the Glycine-Alanine repeats, the control protein and recombinant protein are identical. In some embodiments, the immune response is a humoral response and/or cellular immune response specific for the recombinant protein. In some embodiments, the lower immune response persists for at least 2, 3, 4, 5, 6, 7, 8, 9, 10, 11, 12, 14, 15, 16 or more weeks. In some embodiments, the immune response is at least 1.5 fold, at least 2 fold, at least 3 fold, at least 4 fold, at least 5 fold, or at least 10 fold lower against the recombinant protein comprising the Glycine-Alanine repeats compared with the control protein.

BRIEF DESCRIPTION OF DRAWINGS

FIG. 6A provides a schematic diagram of OVA expressing cassettes flanked by AAV inverted terminal repeats (ITR). miRBS: miRNA binding sites; GAr: Gly-Ala repeats. FIG. 6B shows that incorporating miR-142 and/or miR-155 binding sites significantly inhibited OVA expression in mouse dendritic cells or macrophages. JAWS II or RAW264.7 cells were seeded into 24-well plated and transfected with corresponding plasmids (1 µg/well), 24 hours after transfection supernatant were collected for OVA ELISA. FIG. 6C shows in vitro CTL assays. JAWS II cells were transfected with plasmids (1 µg/1E6 cells/well, 24-well plate). Two days after transfection, OT-1 specific CD8+ T cells (B3Z T) were added (1E6 cells/well). Following 18-hour co-culture, the cells were harvested and lysed for β-galactosidase analysis. FIG. 6D shows in vivo CTL assays. Six-week-old mice were injected with PBS, rAAV1.OVA, rAAV1.OVA.8GA and rAAV1.OVA.miR(142+155)BS (1e11 GC/mouse. i.m.). Seventeen days after injection, target cells from the spleen of the same strain of naive mice were either labeled with high concentration of CFSE (CFSEhi, 5 µM) and pulsed with SIINFEKL peptide (OT-1, 1 µg/mL) or labeled with a low concentration of CFSE (CFSE lo, 0.5 µM) and not pulsed. The populations of target cells were mixed (1:1) and co- transferred intravenously (4e7 cells). Six hours later, splenocytes were isolated and analyzed by flow cytometry to determine the percentage of remaining target cells. The percent specific killing was calculated, as shown in FIG. 6E, with *p<0.05 and ***p<0.001 for a one-way ANOVA followed by Tukey's test.

DETAILED DESCRIPTION

Figure 1:
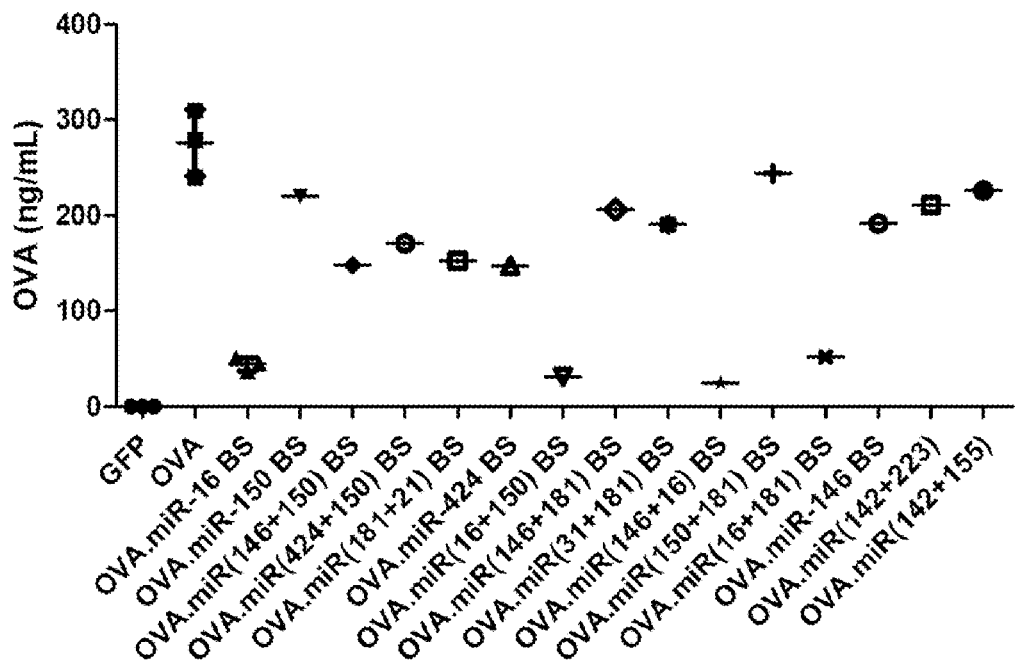
FIG. 1. Detection of AAV-based OVA expression from constructs with and without immune-associated miRNA binding sites in HEK-293 cells. HEK293 cells were cultured into 24-well plates for 24 hours and then transfected with corresponding plasmids (500 ng/well). Twenty-four hours after transfection, supernatants were collected for OVA ELISA assay.
Figure 2:
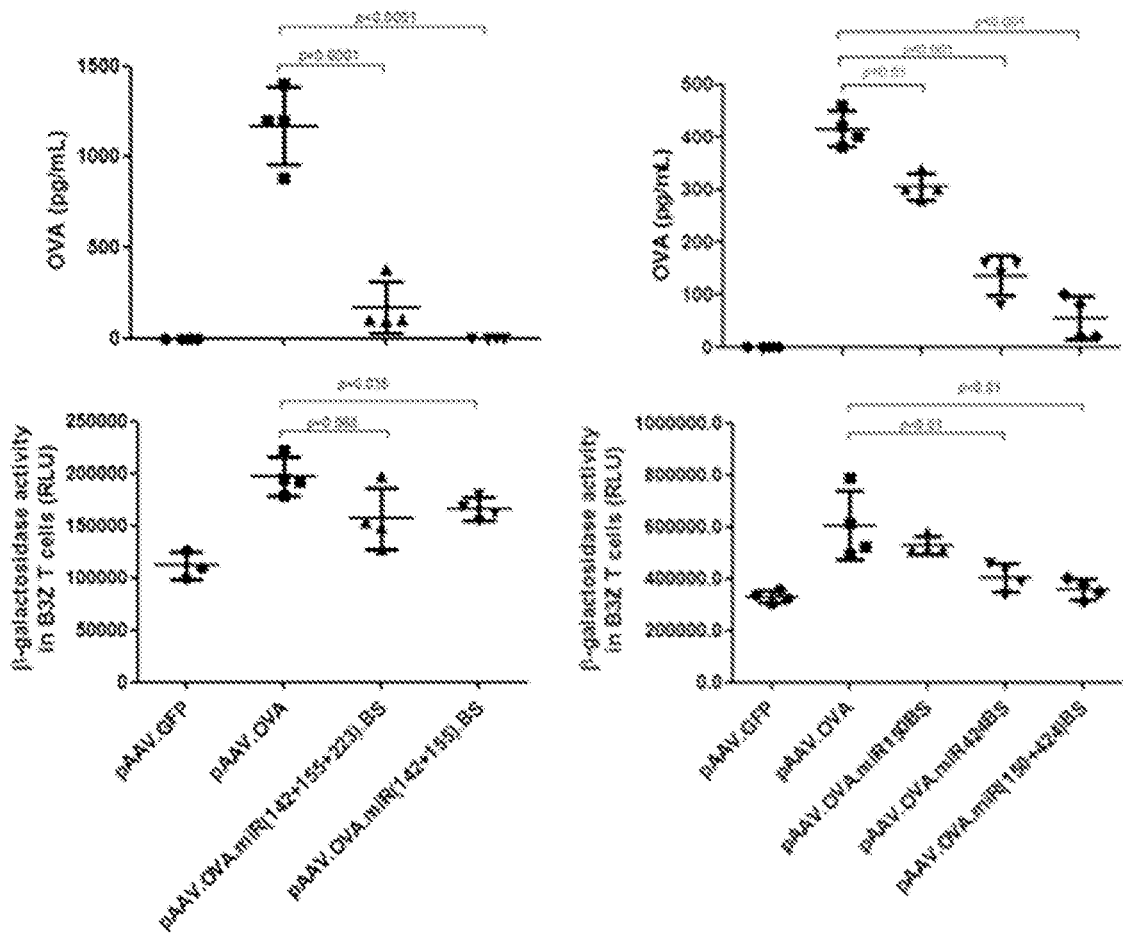
FIG. 2. miRNA-regulated transgene expression in Dendritic cell lines. JAWS II cells (ATCC, CRL-11904) were cultured in Alpha minimum essential medium with ribonucleosides, deoxyribonucleosides, 4 mM L-glutamine, 1 mM sodium pyruvate and 20% FBS with 5 ng/ml murine GM-CSF. 1E6 cells were collected and transfected with corresponding plasmids (pAAV.GFP, pAAV.OVA.and pAAV.OVA.miR.BS 2x). 24 hours after transfection, collect the supernatant for OVA ELISA assay. 3 days after transfection, OT-1 specific CD8+ T cells (B3Z T) were added (1E6 cells/well). Following 18-hour co-culture, the cells harvested and lysed for β-galactosldase analysis (ABI β-gal assay kit).
Figure 2:
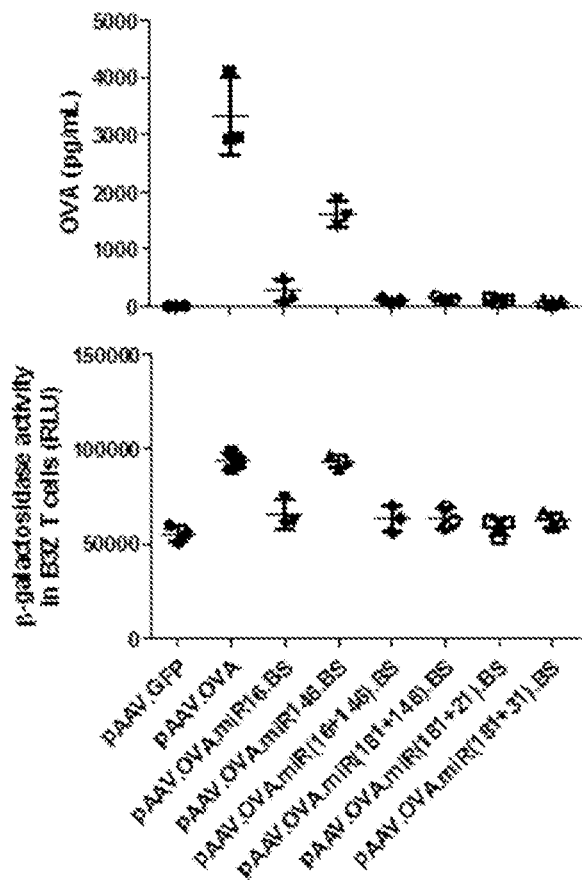
Figure 3:
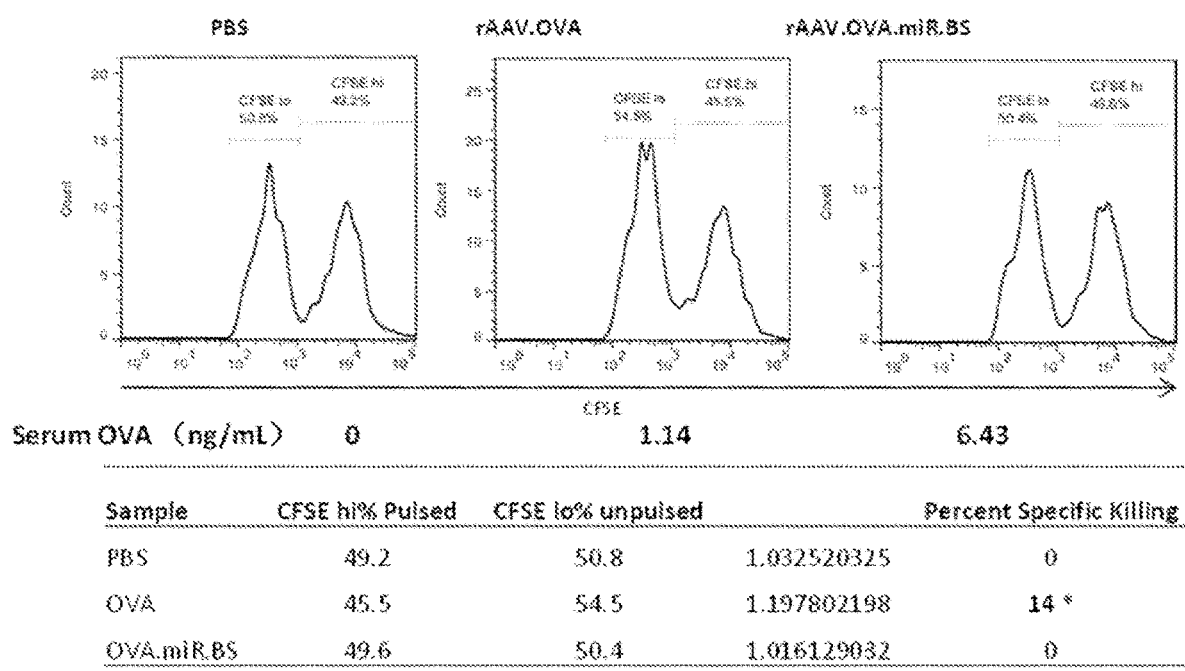
FIG. 3 In vivo CTL assay. Six-week-old mice were injected with PBS, rAAV.OVA. and rAAV.OVA.miR142BS+ miR155BS(1E11 GC/mouse. Intramuscularly (IM)). Day 17 after injection, target cells from the spleen of the same strain of mouse were either labeled with high concentration of CFSE (CFSEhi, 10 µM) and pulsed with SIINFEKL peptide (OT-1, 1 µg/mL) or labeled with a low concentration of CFSE (CFSElo, 0.5 µM) and not pulsed. The populations of target cells were mixed (1:1) and cotransferred intravenously (4E7 cells). Six hours later, splenocytes were isolated and analyzed by flow cytometry to determine the percentage of remaining target cells.
Figure 4:
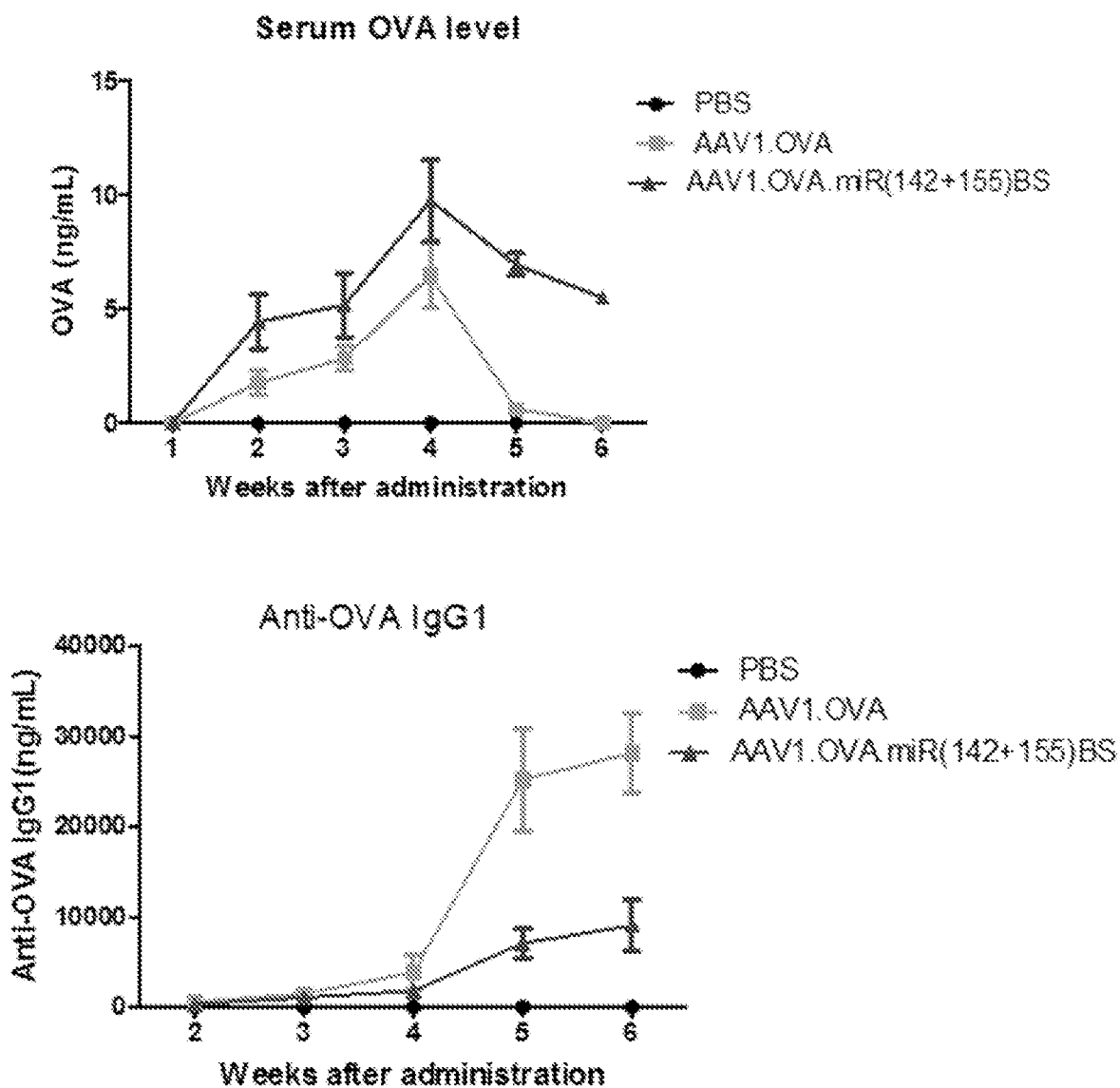
FIG. 4. Incorporating miRNA binding sites prolongs transgene expression with decreased IgG1 level. Six-week-old C57BL/6 male mice were injected (IM) with PBS, AAV1.CB6.OVA or AAV1.CB6.OVA.miR(142+155)BS2x (1e11 GC/mouse, n=5/group). Sera were collected at different time points for serum OVA protein and OVA-specific IgG1 (ELISA) analysis. The top and bottom panel show the results of two independent experiments.
Figure 4:
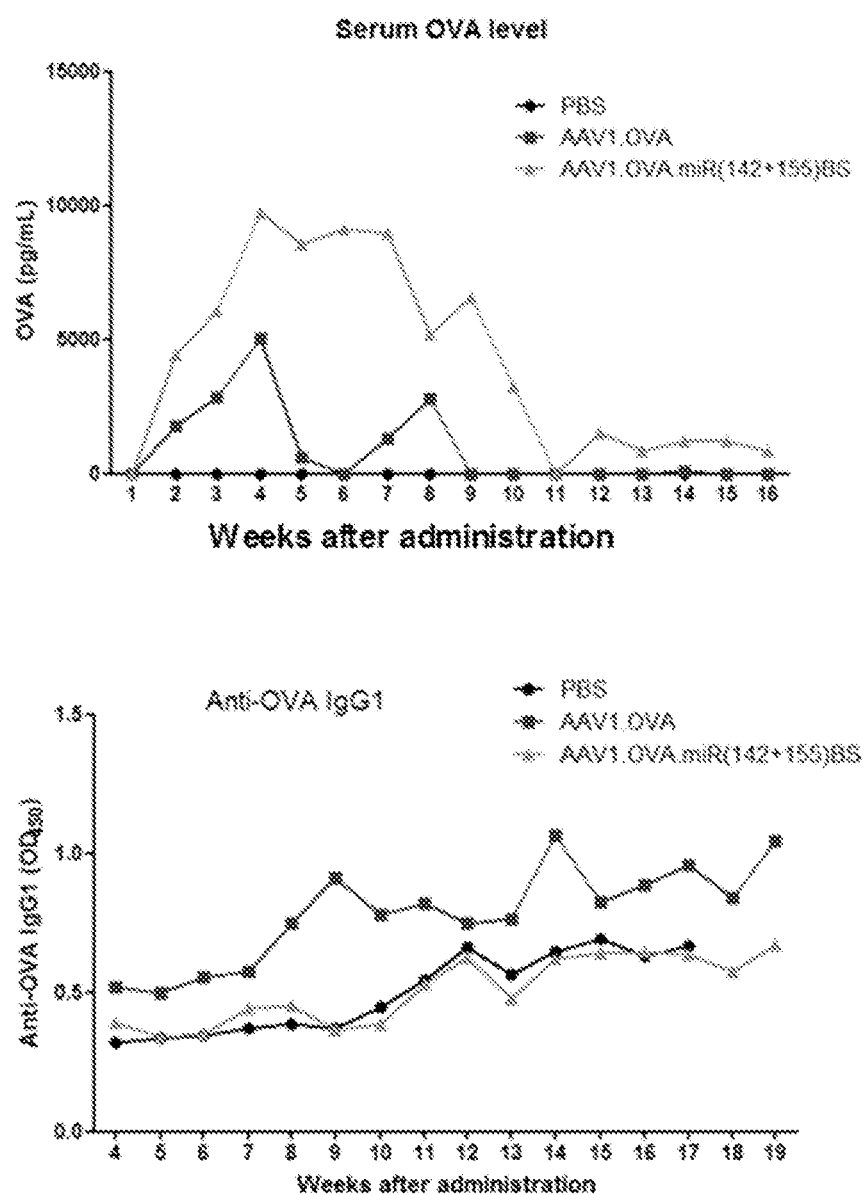
Figure 5:
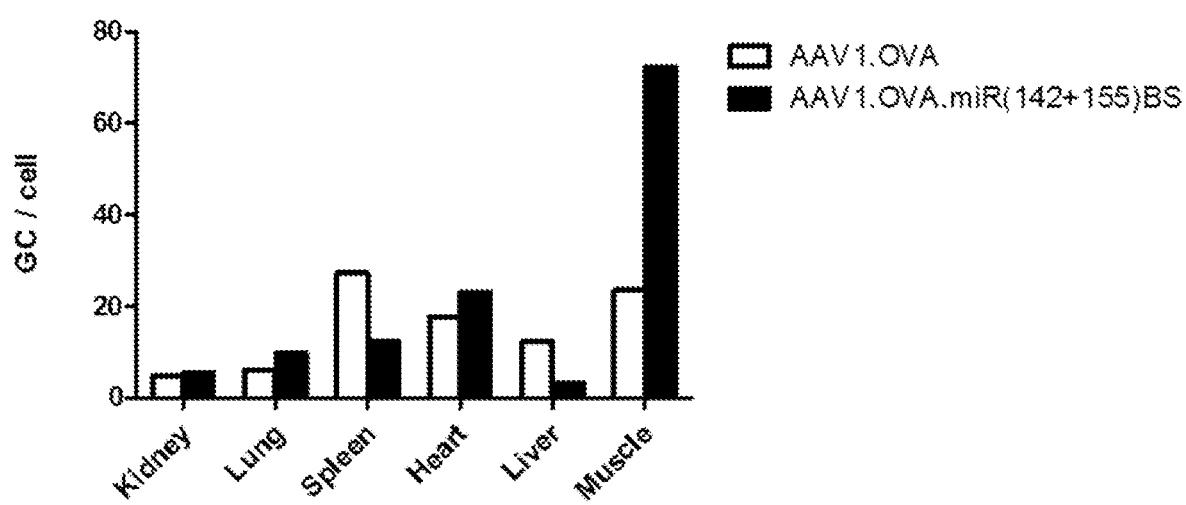
FIG. 5. Biodistribution of AAV1 vectors in mice. Six-week-old C57BL/6 mice were injected AAV1.OVA or AAV1.OVA.miR (142+155)BS (1E11 GC/mouse, tibialis anterior (T.A.) muscle injection). Five weeks after injection, organs were collected for qPCR analysis.
Figure 6A:
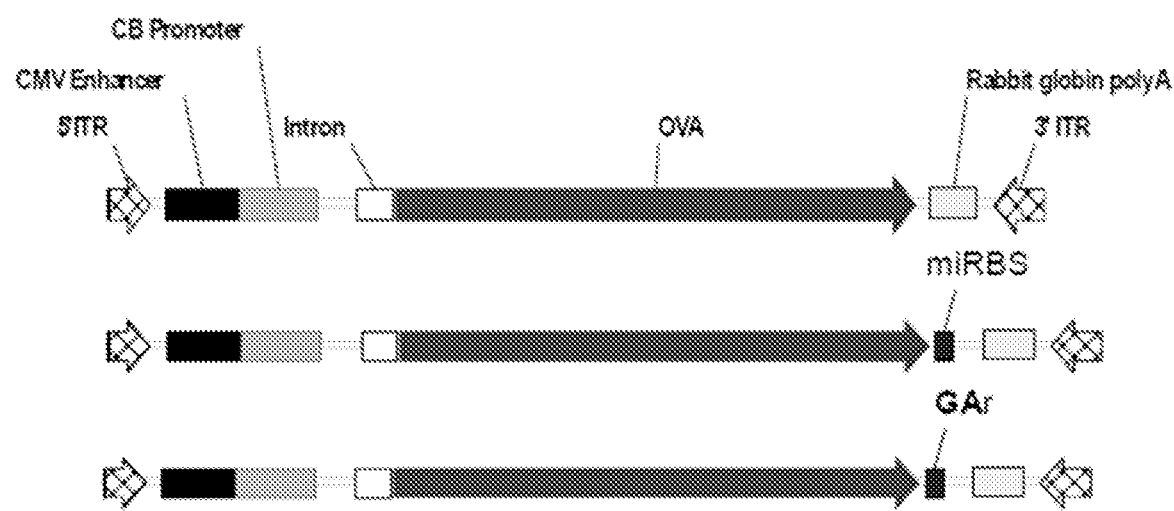
FIGS. 6A-6E illustrate results showing that incorporation of miRNA binding sites or GA repeats reduced OVA-specific CTL activity in vitro and in vivo.
Figure 6B:
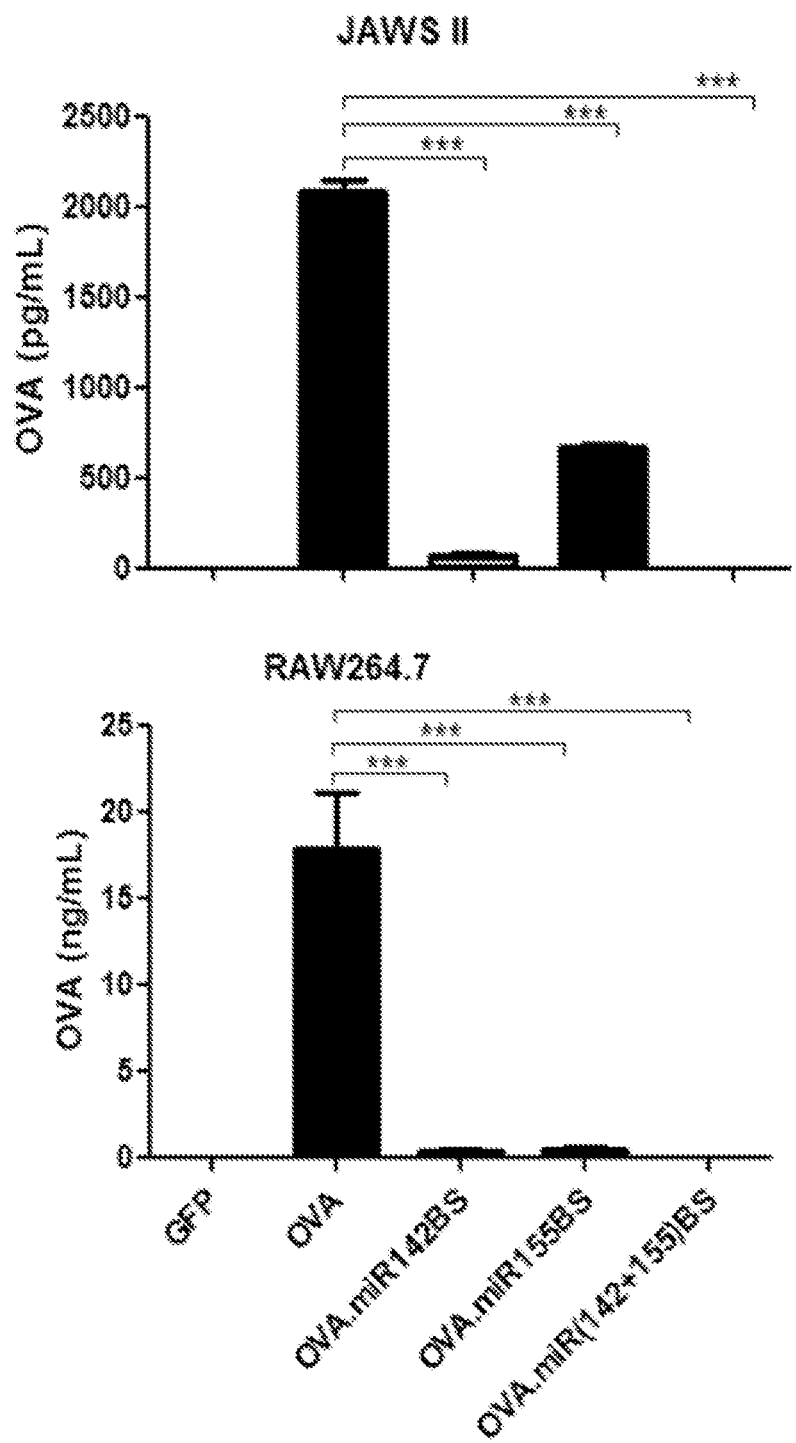
Figure 6C:
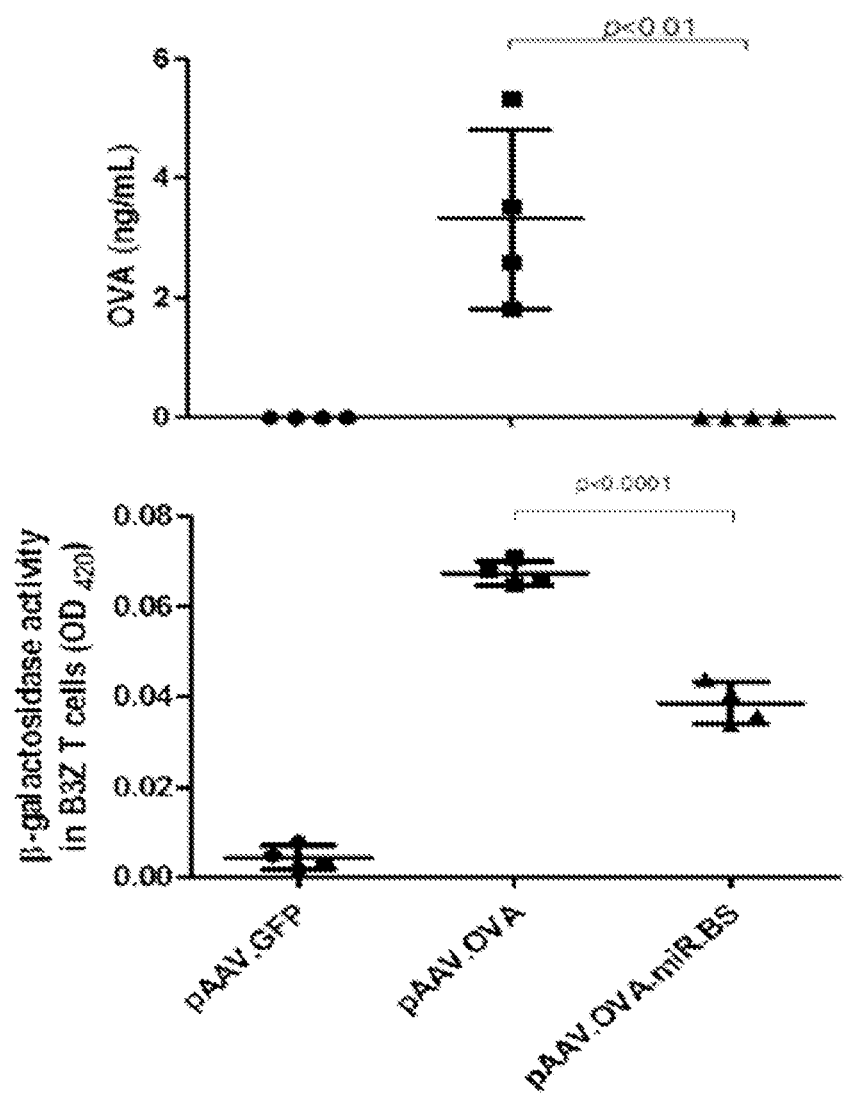
Figure 6D:
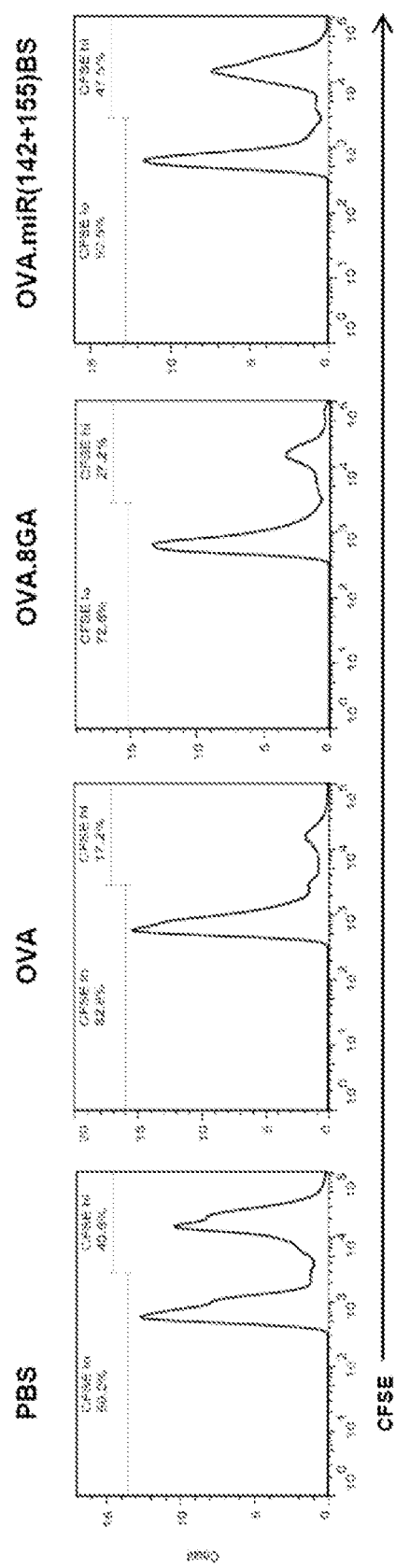
Figure 6E:
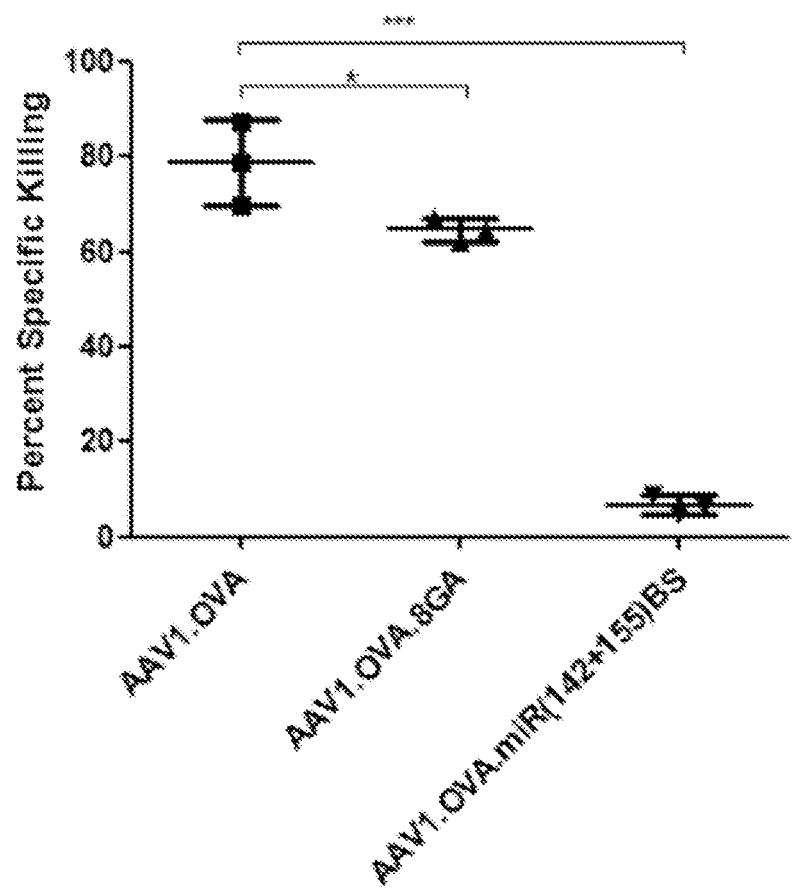
Figure 7A:
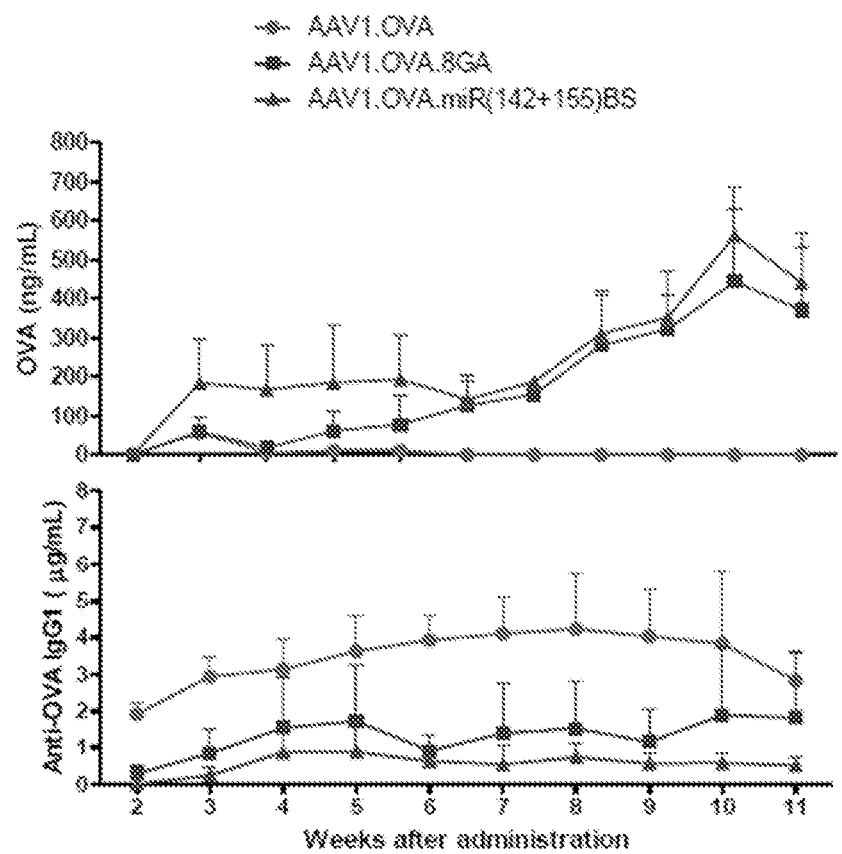
FIGS. 7A-7D depicts that incorporating miR(142+155) binding sites or GA repeats results in sustained OVA protein level with decreased anti-OVA IgG1 level in vivo. Six-week-old mice were injected with PBS, rAAV1.OVA, rAAV1.OVA.8GA and rAAV1.OVA.miR(142+155)BS (1e11 GC/mouse. i.m.). Sera were collected at different time points for OVA protein and anti-OVA IgG1 (ELISA) analysis, as shown in FIG. 7A. Three weeks after injection, the splenocytes were isolated and stimulated with or without OVA for perforin expression analysis by flow cytometry, as show in FIG. 7B. The sera were collected for cytokine ELISA, as shown in FIG. 7C, and the injected skeletal muscle was harvested for HE staining, as shown in FIG. 7D. For the cytokine analyses depicted in FIG. 7C in the top panel, the bars show for each injection condition, from left to right, levels of IL-2, IL-4, IL-5, IL-10, IL-12, GM-CSF, and IFN-γ. The lower panel in FIG. 7C shows levels of TNF-α for each injection condition.
Figure 7B:
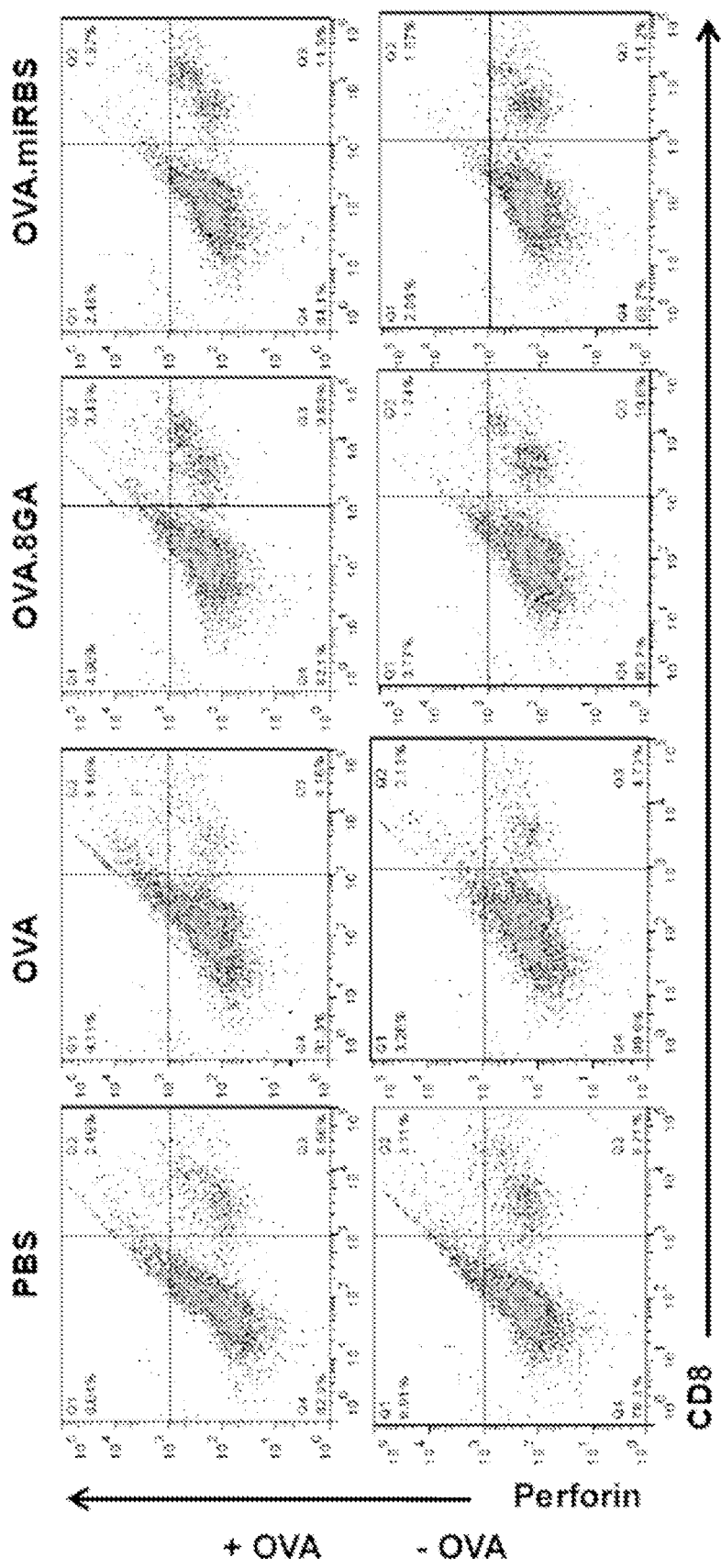
Figure 7C:
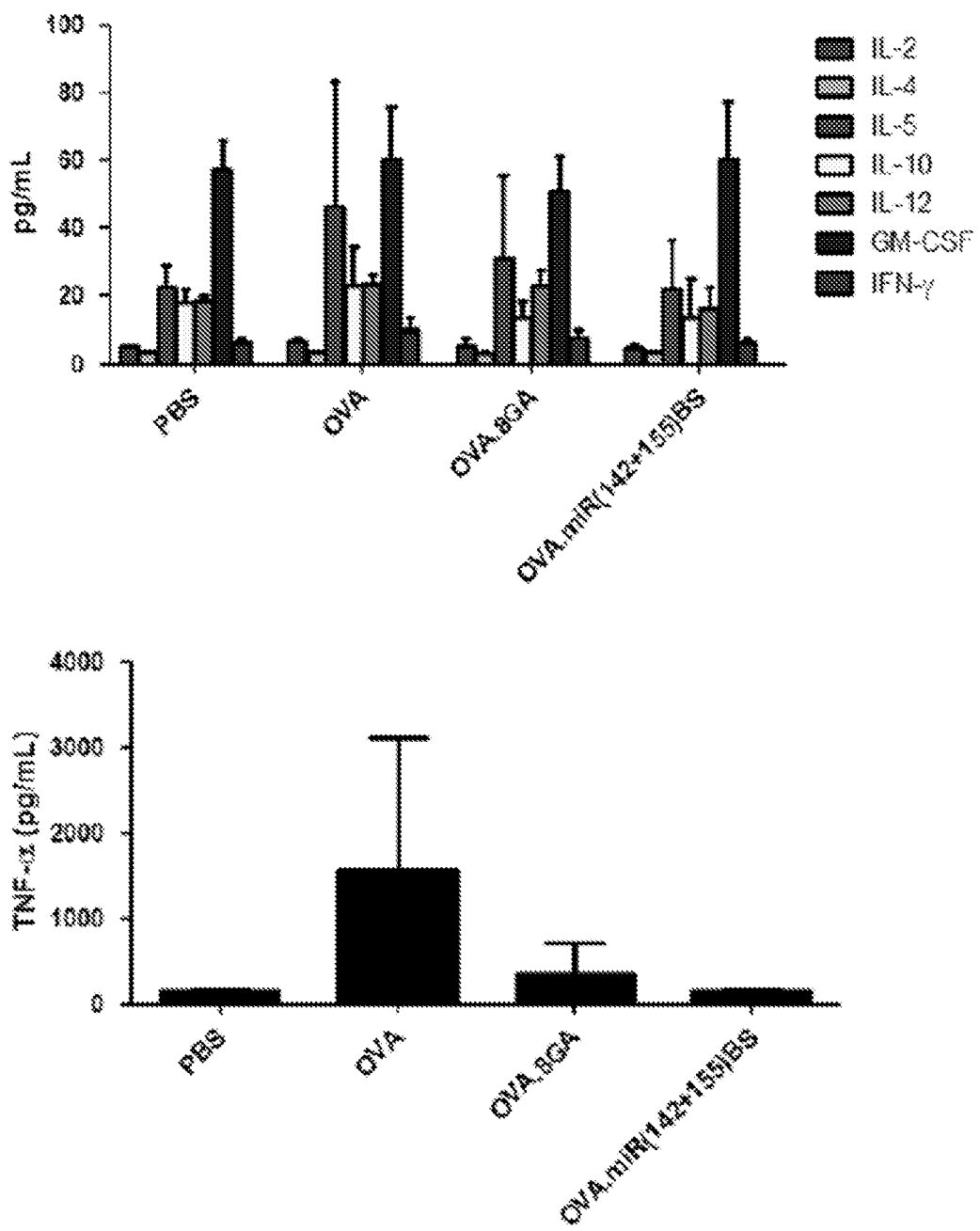
Figure 7D:
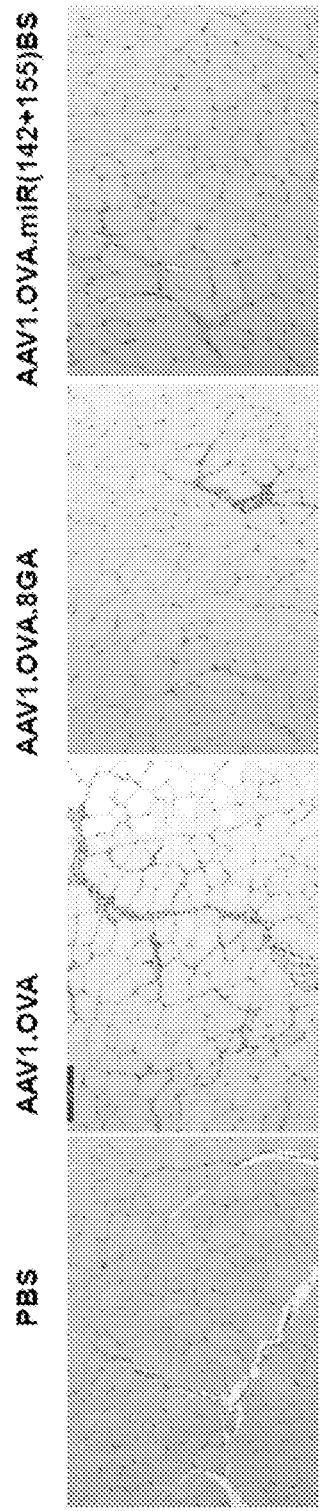

Aspects of the disclosure relate to a recognition that immune responses can occur that are directed against therapeutic transgene products delivered by recombinant adeno-associated viruses (rAAVs), which can lead to untoward outcomes. In some cases, for example, a B cell response to a transgene product results in inhibitory antibodies, thereby impairing the treatment. Accordingly, aspects of the disclosure relate to methods of delivering a transgene to target cells of a subject in a manner that reduces or eliminates immune responses (cellular and/or humoral) produced in the subject against products of the transgene. In some embodiments, the use of recombinant AAVs to deliver transgenes is disclosed. Also described herein are transgenes engineered with combinations of different immune-related miRNA binding sites to achieve synergistic effects. AAV is advantageous for gene therapy due to lack of pathogenicity, lower immunogenicity and ability to establish long-term transgene expression. In some embodiments, advantages of AAV are combined with immune-associated miRNA-regulated transgene expression to overcome immune responses against transgene products. In some embodiments, methods are provided that involve administering to the subject a recombinant Adeno-Associated Virus (rAAV) that harbors a transgene engineered to express an RNA transcript that comprises a binding site of at least one immune-associated miRNA (e.g., an immune-associated miRNA of Table 1). In some embodiments, to reduce immune responses against rAAV-derived transgene products, AAV vectors are provided that incorporate immune-related miRNA binding sites (BS) into the 3'UTR of the transgene. In some aspects, the miRNA binding sites are the reverse complement of specific miRNAs expressed in immune cells, as disclosed herein. In some aspects, the miRNA binding sites function to reduce the presentation of transgenes through the antigen presentation pathways.

In some embodiments, presence of binding sites of one or more immune-associated miRNAs results in a lower immune response in a subject against a product of the RNA transcript compared with an appropriate control. An appropriate control can be a predetermined level indicative of an undesirable immune response. In some embodiments, an appropriate control is the level of an immune response in a control subject that has been administered a control rAAV comprising a transgene engineered to express a control RNA transcript encoding the product, wherein the control RNA transcript does not comprise immune-associated miRNA binding sites. For example, the lower immune response may be i) a lower level of antibodies specific for the product of the transgene, ii) a lower level of T-lymphocytes specific for the product, or iii) a lower level of antigen presenting cells in the subject that display antigens of the product through MHC class I molecules. The immune response may be less than 10%, less than 20%, less than 30%, less than 40%, less than 50%, less than 60%, less than 70%, less than 80%, or less than 90% of the appropriate control level, for example. It should be appreciated that the immune response may be sufficiently low so as to permit the product of the transgene to perform its intended function. It should also be appreciated that immune response may be sufficiently low so as to permit the product of the transgene to perform its desired therapeutic effect in the subject.

MicroRNAs (miRNAs) are small, non-coding RNAs which regulate cellular gene expression by post-transcriptional silencing. When miRNAs are partially complementary to the target mRNA sequences, they typically reduce target mRNA stability and inhibit translation. In contrast, when miRNAs are nearly perfectly complementary to their mRNA targets, they cleave the mRNA, triggering its wholesale destruction. miRNA can achieve tissue specific regulation of systemically delivered and ubiquitously expressed transgenes at post-transcriptional level. miRNAs have distinct expression profiles in different tissues and cell types, which differentially regulate transcriptional profiles of cellular genes and cellular functions, including APCs and immune activation. Therefore, methods provided herein employ immune-related miRNAs (e.g., APC-specific miRNAs) to silence transgene expression in immune cells (e.g., APCs). Accordingly, methods provided herein reduce immune responses to transgene products. As used herein an "immune-associated miRNA" is an miRNA preferentially expressed in a cell of the immune system, such as an antigen presenting cell (APC). In some embodiments, an immune-associated miRNA is an miRNA expressed in immune cells that exhibits at least a 2-fold, 3-fold, 4-fold, 5-fold, 6-fold, 7-fold, 8-fold, 9-fold, 10-fold higher level of expression in a immune cell compared with a non-immune cell (e.g., a control cell, such as a HeLa cell, HEK293 cell, mesenchymal cell, etc.). In some embodiments, the cell of the immune system (immune cell) in which the immune-associated miRNA is expressed is a B cell, T cell, Killer T cell, Helper T cell, γδ T cell, dendritic cell, macrophage, monocyte, vascular endothelial cell. or other immune cell. In some embodiments, the cell of the immune system is a B cell expressing one or more of the following markers: B220, BLAST-2 (EBVCS), Bu-1, CD19, CD20 (L26), CD22, CD24, CD27, CD57, CD72, CD79a, CD79b, CD86, chB6, D8/17, FMC7, L26, M17, MUM-1, Pax-5 (BSAP), and PC47H. In some embodiments, the cell of the immune system is a T cell expressing one or more of the following markers: ART2, CD1a, CD1d, CD11b (Mac-1), CD134 (OX40), CD150, CD2, CD25 (interleukin 2 receptor alpha), CD3, CD38, CD4, CD45RO, CD5, CD7, CD72, CD8, CRTAM, FOXP3, FT2, GPCA, HLA-DR, HML-1, HT23A, Leu-22, Ly-2, Ly-m22, MICG, MRC OX 8, MRC OX-22, OX40, PD-1 (Programmed death-1), RT6, TCR (T cell receptor), Thy-1 (CD90), and TSA-2 (Thymic shared Ag-2). In some embodiments, the immune-associated miRNA is selected from: miR-15a, miR-16-1, miR-17, miR-18a, miR-19a, miR-19b-1, miR-20a, miR-21, miR-29a/b/c, miR-30b, miR-31, miR-34a, miR-92a-1, miR-106a, miR-125a/b, miR-142-3p, miR-146a, miR-150, miR-155, miR-181a, miR-223 and miR-424, miR-221, miR-222, let-7i, miR-148, and miR-152. In some embodiments, the immune-associated miRNA is in Table 1.

Another non-limiting example of the usefulness of the constructs of the instant disclosure is the prevention of autoimmune disease. Incorporating immune-related miRNA binding sites into AAV-based constructs may reduce both T cell and B cell responses. A number of autoimmune diseases are mediated by autoantibodies. In some cases, the delayed-type hypersensitivity (DTH) response and auto-reactive CTL responses also contribute to the development of autoimmune diseases.

Additionally, dysregulated miRNA expression may contribute to autoimmune diseases by acting in immune and tissue resident cells. Non-limiting examples include miR-21 and miR-148a, which promote autoimmunity in patients with systemic lupus erythematosus (SLE). miR-31 expression was increased during the progression of inflammatory bowel disease (IBD). miR-155 was found to be up-regulated in synovial membrane and synovial fluid (SF) macrophages from patients with rheumatoid arthritis (RA). miR-17-5p expression was up-regulated in CD4+ lymphocytes of patients with multiple sclerosis (MS). The higher expression of miR-17-92 may promote lymphomagenesis.

Thus, in some embodiments, transgenes may be engineered to express a protein of interest, e.g., a therapeutic protein, such as insulin, and a miRNA inhibitor that blocks activity of autoimmune promoting miRNAs. Transcripts expressing such proteins may also be engineered to contain one or more immune-related miRNAs. In this way, the transcript, if expressed in immune cells, may be degraded via miRNAs expressed in the immune cells. In the same immune cells, the transgene may express miRNA inhibitors that target miRNAs that contribute to autoimmune disease, such as miR-21, miR-148a, miR-31, miR-155, miR-17-5p, and miR-17-92. A "miRNA Inhibitor" is an agent that blocks miRNA function, expression and/or processing. For instance, these molecules include but are not limited to microRNA specific antisense, microRNA sponges, tough decoy RNAs (TuD RNAs) and microRNA oligonucleotides (double-stranded, hairpin, short oligonucleotides) that inhibit miRNA interaction with a Drosha complex. MicroRNA inhibitors can be expressed in cells from a transgenes of a rAAV vector, as discussed above. MicroRNA sponges specifically inhibit miRNAs through a complementary heptameric seed sequence (Ebert, M. S. Nature Methods, Epub Aug. 12, 2007;). In some embodiments, an entire family of miRNAs can be silenced using a single sponge sequence. TuD RNAs achieve efficient and long-term-suppression of specific miRNAs in mammalian cells (See, e.g., Takeshi Haraguchi, et al., Nucleic Acids Research, 2009, Vol. 37, No. 6 e43, the contents of which relating to TuD RNAs are incorporated herein by reference). Other methods for silencing miRNA function (derepression of miRNA targets) in cells will be apparent to one of ordinary skill in the art. In the present disclosure, the incorporated miRNA binding sites and/or expression of miRNA inhibitors may disturb the normal expression profiles the corresponding miRNAs. Therefore, those up-regulated miRNA in the progression of autoimmune diseases could be regulated by AAV-mediated miRNA binding sites or sponge delivery.

In some embodiments, the transgene product is a protein comprising a plurality of Glycine-Alanine repeats (e.g., 2 to 10, 2 to 20, 5 to 10, 5 to 20, 10 to 20, 20 to 50, 10 to 100, 100 to 200 GA repeats) that inhibit proteasomal processing in cells thereby inhibiting antigen presentation by MHC class I molecules.

Insulin Delivery

Recombinant AAV vectors have been used to successfully deliver the insulin gene in models of diabetes. The insulin gene was delivered alone or with a glucokinase gene using rAAV vectors. In some embodiments, the insulin gene is delivered alone or with a glucokinase gene using AAV vectors. The present disclosure uses AAV vectors carrying insulin and miRNA binding sites to reduce insulin specific immune responses and addresses regulatory T cells in the insulin immune tolerance. Thus, as a non-limiting example, the destruction of pancreatic β-cells (which secrete insulin) by host immune system is the underlying pathology in the development of type I diabetes (T1D), a disease that often requires a lifelong exogenous insulin replacement therapy. The delivery of adeno-associated virus vectors expressing insulin is an approach provided herein to correct T1D by restoring insulin expression. Dendritic cells induce the immune tolerance when they present β-cell autoantigens to T cells. However, in Type I diabetes, peptides derived from insulin can be presented by MHC class I molecules and recognized by CD8+ T cells. MHC class II molecules expressed by DCs can also present insulin that can induce islet antigen-specific CD4+ T cell expansion. The ability of β-cell autoantigens to activate immature DCs emphasizes their significance as targets for treatment of T1D. Aspects of the disclosure relate to insulin expressing transgenes that incorporate antigen-presenting cell specific miRNA binding sites, resulting in decreased antigen expression and presentation, consequently less antigen-specific T immune responses.

The application of miRNA-mediated detargeting for viral vector-based gene therapy, may also be used for insulin gene transfer to the non-obese diabetic (NOD) mice. Accordingly, the insulin gene may be cloned and incorporated with suitable miRNA binding sites. The constructs may be transfected into non-immune cells (e.g., in HEK293 cells) to evaluate insulin expression (e.g., by ELISA). The constructs may be transfected into mouse dendritic cells to establish the extent to which miRNA binding sites functionally inhibit insulin expression in antigen presenting cells. The constructs may be incorporated into viral vectors (e.g., rAAV1 vectors) and delivered to the non-obese diabetic (NOD) mice which exhibit a susceptibility to spontaneous development of autoimmune insulin dependent diabetes mellitus (IDDM). The extent to which the vectors carrying insulin and miRNA binding sites abrogate diabetes may be determined by evaluating levels of blood glucose, levels of insulin autoantibodies, the extent of pancreatic insulitis and/or the extent of insulin-specific T cell responses.

Recombinant AAV Vectors

"Recombinant AAV (rAAV) vectors" of the disclosure typically comprise a transgene and its regulatory sequences, and 5' and 3' AAV inverted terminal repeats (ITRs). It is this recombinant AAV vector which is packaged into a capsid protein and delivered to a selected target cell. In some embodiments, a transgene comprises a nucleic acid sequence, heterologous to a vector sequences, which encodes a polypeptide, protein, functional RNA molecule (e.g., miRNA sponge) or other gene product of interest. The nucleic acid coding sequence is operatively linked to regulatory components in a manner that permits transgene transcription, translation, and/or expression in a cell of a target tissue.

In some embodiments, nucleic acids are provided that comprise a transgene engineered to express an RNA transcript that comprises binding sites for at least one, at least two or at least three immune-associated miRNAs. In some embodiments, the transgene is flanked by inverted terminal repeat sequences of an adeno-associated virus. In some embodiments, the RNA transcript comprises binding sites for 1, 2, 3, 4, 5, 6, 7, 8, 9, 10, 11, 12, 13, 14, 15, 16, 17, 18, 19, 20, 21, 22, 23, 24, 25 or more immune-associated miRNAs. In some embodiments, the RNA transcript comprises binding sites for a number of immune-associated miRNAs in a range of 1 to 5, 1 to 10, 2 to 5, 2 to 10, 2 to 15, 2 to 20, or 5 to 25 immune-associated miRNAs, which may or may not be selected from Table 1. In some embodiments, the nucleic acid encodes an RNA transcript having at least two immune-associated miRNAs selected from a row of Table 3. In some embodiments, the transgene does not contain a binding site for miR-142. In some embodiments, an immune-associated miRNA binding site is in an exon, intron, intron-exon junction, 5' UTR, or 3' UTR of the RNA transcript.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types.

In addition to the major elements identified above for the recombinant AAV vector, the vector also includes conventional control elements necessary which are operably linked to the transgene in a manner which permits its transcription, translation and/or expression in a cell transfected with the plasmid vector or infected with the virus produced by the disclosure. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (e.g., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., shRNA, miRNA, miRNA inhibitor).

For nucleic acids encoding proteins, a polyadenylation sequence generally is inserted following the transgene sequences and before the 3' AAV ITR sequence. A rAAV vector useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268:1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be used when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, a insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (, Hansal et al., J. Immunol., 161:1063-8 (1998);

immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan. In some embodiments, the promoter is the muscle specific promoter Desmin460 or the truncated muscle creatine kinase (tMCK) promoter.

Recombinant AAVs

AAVs produced using recombinant methods are referred to herein as "recombinant AAVs". Recombinant AAVs (rAAVs) may have tissue-specific targeting capabilities, such that a transgene of the rAAV will target specifically to one or more predetermined tissue(s). The AAV capsid is an important element in determining these tissue-specific targeting capabilities. Thus, an rAAV having a capsid appropriate for the tissue being targeted can be selected. Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein or fragment thereof; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments the rAAV comprises a capsid protein of a serotype selected from: AAV1, AAV2, AAV3, AAV4, AAV5, AAV6, AAV7, AAV8, AAV9, AAV10, AAV11, AAV12, AAV.rh.10 and variants of any one of them. In some embodiments, the rAAV comprises a capsid protein disclosed in United States Patent Application Publication Number US 2012/0137379, entitled, "NOVEL AAV'S AND USES THEREOF," which was published on May 31, 2012, the contents of which are incorporated herein by reference in their entirety. In some embodiments, the capsid protein is modified to contain Gly-Ala repeats of Epstein-Ban virus Nuclear antigen that reduce proteasomal processing of the capsid protein in cells and capsid specific immune responses. In some embodiments, the capsid protein is modified to contain up to 2, up to 3, up to 4, up to 5, up to 10, up to 20, or up to 50 Gly-Ala repeats that reduce proteasomal processing of the capsid protein in cells and capsid specific immune responses.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component (s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

The recombinant AAV vector, rep sequences, cap sequences, and helper functions involved in producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al, J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (e.g., rep and cap), which function in trans for productive AAV replication and encapsidation. Preferably, the AAV helper function vector supports efficient AAV vector production without generating any detectable wild-type AAV virions (e.g., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (e.g., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected.

Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA (e.g., shRNA, miRNA, miRNA inhibitor) from a transcribed gene.

The foregoing methods for packaging recombinant vectors in desired AAV capsids to produce the rAAVs of the disclosure are not meant to be limiting and other suitable methods may be used.

Recombinant AAV Vector: Transgene Coding Sequences

The composition of the transgene sequence of the rAAV vector will depend upon the use to which the resulting vector will be put. For example, one type of transgene sequence includes a reporter sequence, which upon expression produces a detectable signal. In another example, the transgene encodes a therapeutic protein or therapeutic functional RNA. In another example, the transgene encodes a protein or functional RNA that is intended to be used for research purposes, e.g., to create a somatic transgenic animal model harboring the transgene, e.g., to study the function of the transgene product. In another example, the transgene encodes a protein or functional RNA that is intended to be used to create an animal model of disease. Appropriate transgene coding sequences will be apparent to the skilled artisan.

Reporter sequences that may be provided in a transgene include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, Ovalbumin (OVA) and others well known in the art. When associated with regulatory elements which drive their expression, the reporter sequences, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for β-galactosidase activity. Where the transgene is green fluorescent protein or luciferase, the vector carrying the signal may be measured visually by color or light production in a luminometer. Such reporters can, for example, be useful in verifying the tissue-specific targeting capabilities and tissue specific promoter regulatory activity of an rAAV.

In some aspects, the disclosure provides rAAV vectors for use in methods of preventing or treating one or more genetic deficiencies or dysfunctions in a mammal, such as for example, a polypeptide deficiency or polypeptide excess in a mammal, and particularly for treating or reducing the severity or extent of deficiency in a human manifesting one or more of the disorders linked to a deficiency in such polypeptides in cells and tissues. The method involves administration of an rAAV vector that encodes one or more therapeutic peptides, polypeptides, siRNAs, microRNAs, antisense nucleotides, etc. in a pharmaceutically-acceptable carrier to the subject in an amount and for a period of time sufficient to treat the deficiency or disorder in the subject suffering from such a disorder.

Thus, the disclosure embraces the delivery of vectors encoding one or more peptides, polypeptides, or proteins, which are useful for the treatment or prevention of disease states in a mammalian subject. Exemplary therapeutic proteins include one or more polypeptides selected from the group consisting of growth factors, interleukins, interferons, anti-apoptosis factors, cytokines, anti-diabetic factors, anti-apoptosis agents, coagulation factors, anti-tumor factors. Other non-limiting examples of therapeutic proteins include BDNF, CNTF, CSF, EGF, FGF, G-SCF, GM-CSF, gonadotropin, IFN, IFG-1, M-CSF, NGF, PDGF, PEDF, TGF, VEGF, TGF-B2, TNF, prolactin, somatotropin, XIAP1, IL-1, IL-2, IL-3, IL-4, IL-5, IL-6, IL-7, IL-8, IL-9, IL-10, IL-10(187A), viral IL-10, IL-11, IL-12, IL-13, IL-14, IL-15, IL-16 IL-17, and IL-18.

The vectors disclosed herein may comprise a transgene to be transferred to a subject to treat a disease associated with reduced expression, lack of expression or dysfunction of the native gene. Exemplary genes and associated disease states include, but are not limited to: glucose-6-phosphatase, associated with glycogen storage deficiency type 1A; phosphoenolpyruvate-carboxykinase, associated with Pepck deficiency; galactose-1 phosphate uridyl transferase, associated with galactosemia; phenylalanine hydroxylase, associated with phenylketonuria; branched chain alpha-ketoacid dehydrogenase, associated with Maple syrup urine disease; fumarylacetoacetate hydrolase, associated with tyrosinemia type 1; methylmalonyl-CoA mutase, associated with methylmalonic acidemia; medium chain acyl CoA dehydrogenase, associated with medium chain acetyl CoA deficiency; ornithine transcarbamylase, associated with ornithine transcarbamylase deficiency; argininosuccinic acid synthetase, associated with citrullinemia; low density lipoprotein receptor protein, associated with familial hypercholesterolemia; UDP-glucouronosyltransferase, associated with Crigler-Najjar disease; adenosine deaminase, associated with severe combined immunodeficiency disease; hypoxanthine guanine phosphoribosyl transferase, associated with Gout and Lesch-Nyan syndrome; biotinidase, associated with biotinidase deficiency; beta-glucocerebrosidase, associated with Gaucher disease; beta-glucuronidase, associated with Sly syndrome; peroxisome membrane protein 70 kDa, associated with Zellweger syndrome; porphobilinogen deaminase, associated with acute intermittent porphyria; alpha-1 antitrypsin for treatment of alpha-1 antitrypsin deficiency (emphysema); erythropoietin for treatment of anemia due to thalassemia or to renal failure; vascular endothelial growth factor, angiopoietin-1, and fibroblast growth factor for the treatment of ischemic diseases; thrombomodulin and tissue factor pathway inhibitor for the treatment of occluded blood vessels as seen in, for example, atherosclerosis, thrombosis, or embolisms; aromatic amino acid decarboxylase (AADC), and tyrosine hydroxylase (TH) for the treatment of Parkinson's disease; the beta adrenergic receptor, antisense to, or a mutant form of, phospholamban, the sarco(endo)plasmic reticulum adenosine triphosphatase-2 (SERCA2), and the cardiac adenylyl cyclase for the treatment of congestive heart failure; a tumor suppressor gene such as p53 for the treatment of various cancers; a cytokine such as one of the various interleukins for the treatment of inflammatory and immune disorders and cancers; dystrophin or minidystrophin and utrophin or miniutrophin for the treatment of muscular dystrophies; and, insulin for the treatment of diabetes.

The following are further non-limiting examples of proteins that may be encoded by transgenes of the vectors disclosed herein to treat a disease associated with reduced expression, lack of expression or dysfunction of the native gene: a-galactosidase, acid-glucosidase, adiopokines, adiponectin, alglucosidase alfa, anti-thrombin, ApoAV, ApoCII, apolipoprotein A-I (APOA1), arylsulfatase A, arylsulfatase B, ATP-binding cassette transporter A1 (ABCA1), ABCD1, CCR5 receptor, erythropoietin, Factor VIII, Factor VII, Factor IX, Factor V, fetal hemoglobin, beta-globin, GPI-anchored HDL-binding protein (GPI-HBP) I, growth hormone, hepatocyte growth factor, imiglucerase, lecithin-cholesterol acyltransferase (LCAT), leptin, LDL receptor, lipase maturation factor (LMF) 1, lipoprotein lipase, lysozyme, nicotinamide dinucleotide phosphate (NADPH) oxidase, Rab escort protein-1 (REP-1), retinal degeneration slow (RDS), retinal pigment epithelium-specific 65 (RPE65), rhodopsin, T cell receptor alpha or beta chains, thrombopoietin, tyrosine hydroxylase, VEGF, von heldebrant factor, von willebrand factor, and X-linked inhibitor of apoptosis (XIAP).

In some embodiments, The rAAV vectors may comprise a gene encoding an antigen-binding protein, such as an immunoglobulin heavy chain or light chain or fragment thereof, e.g., that may be used for therapeutic purposes. In some embodiments, the protein is a single chain Fv fragment or Fv-Fc fragment. Accordingly, in some embodiments, the rAAV can be used to infect cells are of target tissue (e.g., muscle tissue) to engineer cells of the tissue to express an antigen-binding protein, such as an antibody or fragment thereof. In some embodiments, to generate rAAVs that express the antibodies or antigen binding fragments, cDNAs engineered to express such proteins will be subcloned into an appropriate plasmid backbone and packaged into an rAAV. In some embodiments, the antigen binding protein and/or is an immunoglobulin heavy or light chain of an antibody or antigen binding fragment thereof that binds selectively to a protein listed in the table below:

|    | Full name                         | Abbreviation |
|----|-----------------------------------|--------------|
| 1  | Tumor necrosis factor-alpha       | TNF-α        |
| 2  | Human Epidermal growth factor receptor 1 | HER1   |
| 3  | Human epidermal growth factor receptor 2 | HER2   |
| 4  | vascular endothelial growth factor A | VEGFA    |
| 5  | cytotoxic T lymphocyte antigen-4  | CTLA-4       |
| 6  | B-cell activating factor          | BAFF         |
| 7  | human immunodeficiency virus      | HIV          |
| 8  | CD11a                             | CD11a        |
| 9  | CD20                              | CD20         |
| 10 | CD25                              | CD25         |
| 11 | CD30                              | CD30         |
| 12 | CD33                              | CD33         |
| 13 | CD52                              | CD52         |

The rAAVs of the disclosure can be used to restore the expression of genes that are reduced in expression, silenced, or otherwise dysfunctional in a subject (e.g., a tumor suppressor that has been silenced in a subject having cancer). The rAAVs of the disclosure can also be used to knockdown the expression of genes that are aberrantly expressed in a subject (e.g., an oncogene that is expressed in a subject having cancer).

The skilled artisan will also realize that in the case of transgenes encoding proteins or polypeptides, that mutations that results in conservative amino acid substitutions may be made in a transgene to provide functionally equivalent variants, or homologs of a protein or polypeptide. In some aspects the disclosure embraces sequence alterations that result in conservative amino acid substitution of a transgene. In some embodiments, the transgene comprises a gene having a dominant negative mutation. For example, a transgene may express a mutant protein that interacts with the same elements as a wild-type protein, and thereby blocks some aspect of the function of the wild-type protein.

In some embodiments, the cloning capacity of the recombinant RNA vector may limited and a desired coding sequence may require the complete replacement of the virus's 4.8 kilobase genome. Large genes may, therefore, not be suitable for use in a standard recombinant AAV vector, in some cases. The skilled artisan will appreciate that options are available in the art for overcoming a limited coding capacity. For example, the AAV ITRs of two genomes can anneal to form head to tail concatamers, almost doubling the capacity of the vector. Insertion of splice sites allows for the removal of the ITRs from the transcript. Other options for overcoming a limited cloning capacity will be apparent to the skilled artisan.

Although the disclosure provides rAAVs and related vectors, it should be appreciated that in some embodiments immune-related miRNAs may be engineered into transgenes that are delivered using other vectors, such as, for example, vectors for use with retroviruses, oncoretroviruses, adenoviruses, ONYX-015, Herpes simplex viruses, moloney murine leukemia viruses (MMLV), and vaccinia viruses.

Recombinant AAV Administration Methods

The rAAVs may be delivered to a subject in compositions according to any appropriate methods known in the art. The rAAV, preferably suspended in a physiologically compatible carrier (e.g., in a composition), may be administered to a subject, e.g. host animal, such as a human, mouse, rat, cat, dog, sheep, rabbit, horse, cow, goat, pig, guinea pig, hamster, chicken, turkey, or a non-human primate (e.g, Macaque). In some embodiments a host animal does not include a human.

Delivery of the rAAVs to a mammalian subject may be by, for example, intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the virions into the vasculature of an isolated limb to potentially enhance transduction into muscle cells or tissue. Moreover, in certain instances, it may be desirable to deliver the virions to the CNS of a subject. By "CNS" is meant all cells and tissue of the brain and spinal cord of a vertebrate. Thus, the term includes, but is not limited to, neuronal cells, glial cells, astrocytes, cereobrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, a effective amount of the rAAV is generally in the range of from about 1 ml to about 100 ml of solution containing from about $10^9$ to $10^{16}$ genome copies. In some embodiments, the rAAV transduces hepatocytes. In certain embodiments, the effective amount of rAAV is $10^{10}$, $10^{11}$, $10^{12}$, $10^{13}$, or $10^{14}$ genome copies per kg. In certain embodiments, the effective amount of rAAV is $10^{10}$, $10^{11}$, $10^{12}$, $10^{13}$, $10^{14}$, or $10^{15}$ genome copies per subject. In some cases, a dosage between about $10^{11}$ to $10^{12}$ rAAV genome copies is appropriate. For example, in certain embodiments, $10^{12}$ rAAV genome copies is effective to target heart, liver, and pancreas tissues. In some embodiments, a dose of rAAV for intramuscular injection is $10^{11}$ GC/25 g body weight. In some embodiments, the dosage in the range of $10^{11}$ to $10^{13}$ genome copies per kg.

In some embodiments, rAAV compositions are formulated to reduce aggregation of AAV particles in the composition, particularly where high rAAV concentrations are present (e.g., ~$10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV-based therapeutic constructs in suitably formulated pharmaceutical compositions disclosed herein either subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered trangenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 .ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (ie., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

In some cases, the methods involve transfecting cells with total cellular DNAs isolated from the tissues that potentially harbor proviral AAV genomes at very low abundance and supplementing with helper virus function (e.g., adenovirus) to trigger and/or boost AAV rep and cap gene transcription in the transfected cell. In some cases, RNA from the transfected cells provides a template for RT-PCR amplification of cDNA and the detection of novel AAVs. In cases where cells are transfected with total cellular DNAs isolated from the tissues that potentially harbor proviral AAV genomes, it is often desirable to supplement the cells with factors that promote AAV gene transcription. For example, the cells may also be infected with a helper virus, such as an Adenovirus or a Herpes Virus. In a specific embodiment, the helper functions are provided by an adenovirus. The adenovirus may be a wild-type adenovirus, and may be of human or non-human origin, preferably non-human primate (NHP) origin. Similarly adenoviruses known to infect non-human animals (e.g., chimpanzees, mouse) may also be employed in the methods of the disclosure (See, e.g., U.S. Pat. No. 6,083,716). In addition to wild-type adenoviruses, recombinant viruses or non-viral vectors (e.g., plasmids, episomes, etc.) carrying the necessary helper functions may be utilized. Such recombinant viruses are known in the art and may be prepared according to published techniques. See, e.g., U.S. Pat. Nos. 5,871,982 and 6,251,677, which describe a hybrid Ad/AAV virus. A variety of adenovirus strains are available from the American Type Culture Collection, Manassas, Va., or available by request from a variety of commercial and institutional sources. Further, the sequences of many such strains are available from a variety of databases including, e.g., PubMed and GenBank.

Cells may also be transfected with a vector (e.g., helper vector) which provides helper functions to the AAV. The vector providing helper functions may provide adenovirus functions, including, e.g., E1a, E1b, E2a, E4ORF6. The sequences of adenovirus gene providing these functions may be obtained from any known adenovirus serotype, such as serotypes 2, 3, 4, 7, 12 and 40, and further including any of the presently identified human types known in the art. Thus, in some embodiments, the methods involve transfecting the cell with a vector expressing one or more genes necessary for AAV replication, AAV gene transcription, and/or AAV packaging.

In some cases, a novel isolated capsid gene can be used to construct and package recombinant AAV vectors, using methods well known in the art, to determine functional characteristics associated with the novel capsid protein encoded by the gene. For example, novel isolated capsid genes can be used to construct and package recombinant AAV (rAAV) vectors comprising a reporter gene (e.g., B-Galactosidase, GFP, Luciferase, etc.). The rAAV vector can then be delivered to an animal (e.g., mouse) and the tissue targeting properties of the novel isolated capsid gene can be determined by examining the expression of the reporter gene in various tissues (e.g., heart, liver, kidneys) of the animal. Other methods for characterizing the novel isolated capsid genes are disclosed herein and still others are well known in the art. The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for detecting a latent AAV in a cell. In addition, kits of the disclosure may include, instructions, a negative and/or positive control, containers, diluents and buffers for the sample, sample preparation tubes and a printed or electronic table of reference AAV sequence for sequence comparisons.

EXAMPLES

Example 1: In Vitro Testing of AAV-miRNA Binding Site Constructs

The following examples demonstrates effectiveness of immune-related miRNA sequences for inhibiting expression of transgenes in APCs. Immune-related miRNA species were selected which include but are not limited to miR-15a, miR-16-1, miR-17, miR-18a, miR-19a, miR-19b-1, miR-20a, miR-21, miR-29a/b/c, miR-30b, miR-31, miR-34a, miR-92a-1, miR-106a, miR-125a/b, miR-142-3p, miR-146a, miR-150, miR-155, miR-181a, miR-223 and miR-424.

In Table 1, the source, function and targets of the listed miRNAs are described. The listed miRNAs are involved in the proliferation, differentiation and maturation of dendritic cells, macrophages, monocytes, B cell, T cells or hematopoietic stem cells., The above miRNA binding sites were synthesized and cloned into 3'UTR of ovalbumin (OVA) transgene in the context of AAV vector. Ovalbumin is highly immunogenic for mice and it has been used to study the immune response of mice to rAAV-mediated transgene products.

Two tandem binding sites for each miRNA species were used. Different combinations of miRNA binding sites, e.g., incorporating two different species of miRNA binding sites, were also tested to see if there is a synergistic effect. All the combinations containing any two of the 25 miRNAs (listed above and Table 1) were considered. For example, miR-142BS+miR-155BS, miR-181BS+miR-31BS, miR-125BS+miR-34BS, etc. In total, there are 300 combinations, as listed in Table 3.

Additionally, different miRNA binding sites which work with high efficiency may be combined in the same transgene. For example, miR-142BS, miR-150BS, or miR-34aBS each work efficiently, and all the three miRNA binding sites may be combined into one construct. Different miRNA binding sites that work in different cell types may also be combined. For instance, miR-155BS works efficiently in dendritic cells and miR-181BS works efficiently in B-cells. Thus, the two miRNA binding sites may be combined in one construct to achieve detargeting in multiple immune cells.

The constructs described above were tested in vitro by transfecting those constructs into primary C57BL/6 mouse dendritic cells or dendritic cell lines (JAWS II, ATCC, CRL-1194). Transgene expression level was determined by enzyme-linked immunosorbent assay (ELISA). The antigen presentation and Cytotoxic-T-Lymphocyte (CTL) activity were analyzed by co-culturing dendritic cells and OVA-specific B3Z T cell line. B3Z T cells contain lacZ that is induced upon engagement of its TCR recognizing OVA peptide (SIINFEKL) in the context of H2Kb. Incorporation of immune-associated miRNAs binding sites significantly decreased transgene expression level in dendritic cells but not in HEK293 cells except miR-16 binding sites (FIG. 1 and FIG. 2). As HEK293 cells have rich endogenous miRNA-16, the vector containing OVA and miR-16 binding sites has reduced OVA expression level compared with the vector carrying OVA alone. By incorporating immune-related miRNA binding sites into OVA also significantly reduced the OVA specific CTL activities in vitro (FIG. 2).

Example 2: In Vivo Testing of AAV-miRNA Binding Site Constructs

AAV vectors containing OVA with and without miRNA binding sites were injected into mice intramuscularly. Incorporating the immune-related miRNA binding sites prolonged the transgene expression (FIG. 4) as well as reduced CTL activity (FIG. 3) and antigen-specific IgG1 antibodies (FIG. 4). The mice intramuscularly injected with AAV1 vectors containing OVA and miRNA binding sites maintained higher AAV vector bio-distribution in the muscles (FIG. 5). As AAV1-mediated antigen expression elicits CD8+ CTL activity, these CTLs may eliminate AAV-transduced muscle cells in mice. However, by incorporating miRNA binding sites into transgene, the CTL activity against AAV-transduced muscle cells was reduced. Therefore the AAV vectors maintained in the muscle cells. In summary, by incorporating immune-related miRNA binding sites may prolong transgene expression with reduced immune responses against transgene products.

Example 3: Incorporating Antigen-Presenting Cell Specific miRNA Binding Sites and/or GA Repeats into AAV Expression Cassettes Result in Sustained Transgene Expression with Decreased Antibodies Against the Transgene Product As disclosed herein, molecular mechanisms that detarget transgene expression from antigen presenting cells (APCs) and/or prevent transgene products from proteasomal degradation and MHC class I presentation by APCs were tested in the context of rAAVs. Endogenous miRNAs were identified and selected that are involved with host immune modulations and conserved across species. Multiple binding sites of those miRNAs (MiRBSs) were engineered in tandem and in different combinations into the 3' UTR of a highly immunogenic transgene, Ovalbumin (Ova) driven by a strong ubiquitous promoter. A library of rAAV.Ova vector plasmids was screened for reduced Ova expression by transfecting mouse macrophage cell line (RAW264.7) or DC lines (JAWS II) and for reduced Cytotoxic-T lymphocyte (CTL) activity by co-culturing the transfected dendritic cells with Ova-specific B3Z T cells containing an Ova responsive LacZ reporter gene. Ova-MiRBS constructs were identified that were expressionally detargeted from DCs and have a diminished CTL response.

Recombinant AAV1 constructs were tested for muscle-directed Ova gene transfer and immunological responses in C57BL/6 mice by in vivo CTL, T and B-cell ELISPOT, intracellular cytokine/cellular marker staining and flow cytometry analysis. In addition, Ova transgene was tagged with Gly-Ala repeats (GAr) from Epstein-Barr virus nuclear antigen 1 (EBNA1). These repeats prevent EBNA1 from proteasomal degradation and MHC class I presentation. This approach was evaluated in vitro and in vivo as disclosed herein. Results with Ova-MiR(142+155)BS and Ova-GAr constructs revealed that, while control rAAV1.Ova elicited cellular and humoral immunities to Ova, causing a transient Ova expression, rAAV1.Ova-MiRBS and rAAV1.Ova-GAr had significantly diminished T and B cell responses to Ova and sustained but different Ova expression profiles.

These results, which are depicted in FIGS. 6 and 7 herein, indicate that incorporating antigen-presenting cell specific miRNA binding sites and/or GA repeats into AAV expression cassettes results in sustained transgene expression with decreased antibodies against the transgene product.

TABLE 1

Summary of Immune-related miRNAs.

| miRNA | Source | Function | Targets |
|---|---|---|---|
| miR-15a/ 16-1 | Monocytes, CD5+ B cells | Negatively controls B cell proliferation; induces TNFα mRNA degradation; Anti-apoptotic | BCL2, TNFα, MCL1, WNT3A CCND1 |
| miR-17~92 cluster (miR-17, -18a, -19a, 20a, -19b-1, -92a-1) | B cells and T cells; Monocytes | Inhibits monocyte proliferation, differentiation and maturation; Regulates pro- to pre- transition during B- and T-cell development | AML-1, Bim, PTEN |
| miR-30b | DC | Promote IL-10 and NO production through targeting Notch1 | Notch1 |
| miR-29a/b/c | T cells | Suppress immune response by targeting IFN-γ | IFN-γ |
| miR-21 | Myeloid cells | Limits immune response-mediated activation of the IL-12/IFN-γ pathway, Th1 polarization | PTEN, PDCD4, IL12A |
| miR-31 | T cells | Regulates IL-2 and kinase suppressor of ras 2 during T cell activation | KSR2 |
| miR-106a | Monocytes | Inhibits monocyte proliferation, differentiation and maturation | AML-1 |
| miR-125a/b | B cells, DC, Monocytes | Negatively regulates TNF-α expression in neonatal monocytes; Reduces apoptosis in immature hematopoietic progenitors | TNFα, Bak1 |
| miR-142-3p | Hematopoietic stem cells, Treg | Prevents Macrophage Differentiation; Regulates cAMP production in Treg. | gp130, C/EBPβ, AC9 |
| miR-146a | Monocytes | Expression induced in macrophages and alveolar/bronchial epithelial following activation of TLR-2, -4 and -5 or exposure to TNFa and IL1b. | IRAK1, TRAF6 |
| miR-150 | B cells and T cells | Increased expression leads to suppression of B-cell formation by blocking in pro- to pre-B cell transition. Decreased expression in chronic lymphocytic leukaemia (CLL) | c-Myb |
| miR-155 | B cells, T cells, macrophages and DCs | Required for normal production of isotype switched, high-affinity IgG1 antibodies in B-cells, determines Th1 and Th2 differentiation and positive regulator of antigen induced responses in T-cells | SHIP1, PU.1, AID, SOCS1, BACH1, CEBPB, CSFR, TAB2, MAF and JARID2 |
| miR-181a | B cells and T cells | Positive regulator of B-cell development and CD4+ T-cell selection, activation and sensitivity. | SHP-2, DUSP5, PTPN22, DUSP6 |
| miR-223 | Myeloid cells | Negative regulator of neutrophil proliferation and activation | Mef2c, IGFR |
| miR-424 | Monocytes | Promoted monocyte differentiation | NFIA, SPI1 |
| miR-34a | DCs and B cells | Promote DC differentiation | Wnt-1 |
| miR-126 | Endothelial cells, pDC | Mediates developmental angiogenesis; Control the survival and function of pDCs | Spred-1 Tsc1 |

TABLE 2

Sequences of miRNA binding sites.

| miRNA | miRNA Binding Sites Sequence (Reverse Complement of miRNA guide strand sequence) | SEQ ID NO: |
|---|---|---|
| miR-15a | CACAAACCATTATGTGCTGCTA | 1 |
| miR-16-1 | CGCCAATATTTACGTGCTGCTA | 2 |
| miR-17 | CTACCAGCACTGTAAGCACTTTG | 3 |
| miR-18a | CTATCTGCACTAGATGCACCTTA | 4 |
| miR-19a | TCAGTTTTGCATAGATTTGCACA | 5 |
| miR-20a | CTACCTGCACTATAAGCACTTTA | 6 |
| miR-19b-1 | GCTGGATGCAAACCTGCAAAACT | 7 |
| miR-21 | TCAACATCAGTCTGATAAGCTA | 8 |
| miR-29a | TAACCGATTTCAGATGGTGCTA | 9 |
| miR-29b | AACACTGATTTCAAATGGTGCTA | 10 |
| miR-29c | TAACCGATTTCAAATGGTGCTA | 11 |
| miR-30b | AGCTGAGTGTAGGATGTTTACA | 12 |
| miR-31 | CAGCTATGCCAGCATCTTGCCT | 13 |
| miR-34a | ACAACCAGCTAAGACACTGCCA | 14 |
| miR-92a-1 | AGCATTGCAACCGATCCCAACCT | 15 |
| miR-106a | CTACCTGCACTGTAAGCACTTTT | 16 |

TABLE 2-continued

Sequences of miRNA binding sites.

| miRNA | miRNA Binding Sites Sequence (Reverse Complement of miRNA guide strand sequence) | SEQ ID NO: |
|---|---|---|
| miR-125a | TCACAGGTTAAAGGGTCTCAGGGA | 17 |
| miR-126 | CGCATTATTACTCACGGTACGA | 18 |
| miR-125b | TCACAAGTTAGGGTCTCAGGGA | 19 |
| miR-142-3p | TCCATAAAGTAGGAAACACTACA | 20 |
| miR-146a | AACCCATGGAATTCAGTTCTCA | 21 |
| miR-150 | CACTGGTACAAGGGTTGGGAGA | 22 |
| miR-155 | ACCCCTATCACAATTAGCATTAA | 23 |
| miR-181a | ACTCACCGACAGCGTTGAATGTT | 24 |
| miR-223 | TGGGGTATTTGACAAACTGACA | 25 |
| miR-424 | TTCAAAACATGAATTGCTGCTG | 26 |

TABLE 3 miRNA Binding Site Pairs

| Binding Site 1 | Binding Site 2 |
|---|---|
| miR-15a | miR-16-1 |
| miR-15a | miR-17 |
| miR-15a | miR-18a |
| miR-15a | miR-19a |
| miR-15a | miR-20a |
| miR-15a | miR-19b-1 |
| miR-15a | miR-21 |
| miR-15a | miR-29a |
| miR-15a | miR-29b |
| miR-15a | miR-29c |
| miR-15a | miR-30b |
| miR-15a | miR-31 |
| miR-15a | miR-34a |
| miR-15a | miR-92a-1 |
| miR-15a | miR-106a |
| miR-15a | miR-125a |
| miR-15a | miR-126 |
| miR-15a | miR-125b |
| miR-15a | miR-142-3p |
| miR-15a | miR-146a |
| miR-15a | miR-150 |
| miR-15a | miR-155 |
| miR-15a | miR-181a |
| miR-15a | miR-223 |
| miR-15a | miR-424 |
| miR-16-1 | miR-17 |
| miR-16-1 | miR-18a |
| miR-16-1 | miR-19a |
| miR-16-1 | miR-20a |
| miR-16-1 | miR-19b-1 |
| miR-16-1 | miR-21 |
| miR-16-1 | miR-29a |
| miR-16-1 | miR-29b |
| miR-16-1 | miR-29c |
| miR-16-1 | miR-30b |
| miR-16-1 | miR-31 |
| miR-16-1 | miR-34a |
| miR-16-1 | miR-92a-1 |
| miR-16-1 | miR-106a |
| miR-16-1 | miR-125a |
| miR-16-1 | miR-126 |
| miR-16-1 | miR-125b |
| miR-16-1 | miR-142-3p |
| miR-16-1 | miR-146a |
| miR-16-1 | miR-150 |
| miR-16-1 | miR-155 |
| miR-16-1 | miR-181a |
| miR-16-1 | miR-223 |
| miR-16-1 | miR-424 |
| miR-17 | miR-18a |
| miR-17 | miR-19a |
| miR-17 | miR-20a |
| miR-17 | miR-19b-1 |
| miR-17 | miR-21 |
| miR-17 | miR-29a |
| miR-17 | miR-29b |
| miR-17 | miR-29c |
| miR-17 | miR-30b |
| miR-17 | miR-31 |
| miR-17 | miR-34a |
| miR-17 | miR-92a-1 |
| miR-17 | miR-106a |
| miR-17 | miR-125a |
| miR-17 | miR-126 |
| miR-17 | miR-125b |
| miR-17 | miR-142-3p |
| miR-17 | miR-146a |
| miR-17 | miR-150 |
| miR-17 | miR-155 |
| miR-17 | miR-181a |
| miR-17 | miR-223 |
| miR-17 | miR-424 |
| miR-18a | miR-19a |
| miR-18a | miR-20a |
| miR-18a | miR-19b-1 |
| miR-18a | miR-21 |
| miR-18a | miR-29a |
| miR-18a | miR-29b |
| miR-18a | miR-29c |
| miR-18a | miR-30b |
| miR-18a | miR-31 |
| miR-18a | miR-34a |
| miR-18a | miR-92a-1 |
| miR-18a | miR-106a |
| miR-18a | miR-125a |
| miR-18a | miR-126 |
| miR-18a | miR-125b |
| miR-18a | miR-142-3p |
| miR-18a | miR-146a |
| miR-18a | miR-150 |
| miR-18a | miR-155 |
| miR-18a | miR-181a |
| miR-18a | miR-223 |
| miR-18a | miR-424 |
| miR-19a | miR-20a |
| miR-19a | miR-19b-1 |
| miR-19a | miR-21 |
| miR-19a | miR-29a |
| miR-19a | miR-29b |
| miR-19a | miR-29c |
| miR-19a | miR-30b |
| miR-19a | miR-31 |
| miR-19a | miR-34a |
| miR-19a | miR-92a-1 |
| miR-19a | miR-106a |
| miR-19a | miR-125a |
| miR-19a | miR-126 |
| miR-19a | miR-125b |
| miR-19a | miR-142-3p |
| miR-19a | miR-146a |
| miR-19a | miR-150 |
| miR-19a | miR-155 |
| miR-19a | miR-181a |
| miR-19a | miR-223 |
| miR-19a | miR-424 |
| miR-20a | miR-19b-1 |
| miR-20a | miR-21 |
| miR-20a | miR-29a |
| miR-20a | miR-29b |
| miR-20a | miR-29c |

TABLE 3-continued miRNA Binding Site Pairs

| Binding Site 1 | Binding Site 2 |
|---|---|
| miR-20a | miR-30b |
| miR-20a | miR-31 |
| miR-20a | miR-34a |
| miR-20a | miR-92a-1 |
| miR-20a | miR-106a |
| miR-20a | miR-125a |
| miR-20a | miR-126 |
| miR-20a | miR-125b |
| miR-20a | miR-142-3p |
| miR-20a | miR-146a |
| miR-20a | miR-150 |
| miR-20a | miR-155 |
| miR-20a | miR-181a |
| miR-20a | miR-223 |
| miR-20a | miR-424 |
| miR-19b-1 | miR-21 |
| miR-19b-1 | miR-29a |
| miR-19b-1 | miR-29b |
| miR-19b-1 | miR-29c |
| miR-19b-1 | miR-30b |
| miR-19b-1 | miR-31 |
| miR-19b-1 | miR-34a |
| miR-19b-1 | miR-92a-1 |
| miR-19b-1 | miR-106a |
| miR-19b-1 | miR-125a |
| miR-19b-1 | miR-126 |
| miR-19b-1 | miR-125b |
| miR-19b-1 | miR-142-3p |
| miR-19b-1 | miR-146a |
| miR-19b-1 | miR-150 |
| miR-19b-1 | miR-155 |
| miR-19b-1 | miR-181a |
| miR-19b-1 | miR-223 |
| miR-19b-1 | miR-424 |
| miR-21 | miR-29a |
| miR-21 | miR-29b |
| miR-21 | miR-29c |
| miR-21 | miR-30b |
| miR-21 | miR-31 |
| miR-21 | miR-34a |
| miR-21 | miR-92a-1 |
| miR-21 | miR-106a |
| miR-21 | miR-125a |
| miR-21 | miR-126 |
| miR-21 | miR-125b |
| miR-21 | miR-142-3p |
| miR-21 | miR-146a |
| miR-21 | miR-150 |
| miR-21 | miR-155 |
| miR-21 | miR-181a |
| miR-21 | miR-223 |
| miR-21 | miR-424 |
| miR-29a | miR-29b |
| miR-29a | miR-29c |
| miR-29a | miR-30b |
| miR-29a | miR-31 |
| miR-29a | miR-34a |
| miR-29a | miR-92a-1 |
| miR-29a | miR-106a |
| miR-29a | miR-125a |
| miR-29a | miR-126 |
| miR-29a | miR-125b |
| miR-29a | miR-142-3p |
| miR-29a | miR-146a |
| miR-29a | miR-150 |
| miR-29a | miR-155 |
| miR-29a | miR-181a |
| miR-29a | miR-223 |
| miR-29a | miR-424 |
| miR-29b | miR-29c |
| miR-29b | miR-30b |
| miR-29b | miR-31 |
| miR-29b | miR-34a |
| miR-29b | miR-92a-1 |
| miR-29b | miR-106a |
| miR-29b | miR-125a |
| miR-29b | miR-126 |
| miR-29b | miR-125b |
| miR-29b | miR-142-3p |
| miR-29b | miR-146a |
| miR-29b | miR-150 |
| miR-29b | miR-155 |
| miR-29b | miR-181a |
| miR-29b | miR-223 |
| miR-29b | miR-424 |
| miR-29c | miR-30b |
| miR-29c | miR-31 |
| miR-29c | miR-34a |
| miR-29c | miR-92a-1 |
| miR-29c | miR-106a |
| miR-29c | miR-125a |
| miR-29c | miR-126 |
| miR-29c | miR-125b |
| miR-29c | miR-142-3p |
| miR-29c | miR-146a |
| miR-29c | miR-150 |
| miR-29c | miR-155 |
| miR-29c | miR-181a |
| miR-29c | miR-223 |
| miR-29c | miR-424 |
| miR-30b | miR-31 |
| miR-30b | miR-34a |
| miR-30b | miR-92a-1 |
| miR-30b | miR-106a |
| miR-30b | miR-125a |
| miR-30b | miR-126 |
| miR-30b | miR-125b |
| miR-30b | miR-142-3p |
| miR-30b | miR-146a |
| miR-30b | miR-150 |
| miR-30b | miR-155 |
| miR-30b | miR-181a |
| miR-30b | miR-223 |
| miR-30b | miR-424 |
| miR-31 | miR-34a |
| miR-31 | miR-92a-1 |
| miR-31 | miR-106a |
| miR-31 | miR-125a |
| miR-31 | miR-126 |
| miR-31 | miR-125b |
| miR-31 | miR-142-3p |
| miR-31 | miR-146a |
| miR-31 | miR-150 |
| miR-31 | miR-155 |
| miR-31 | miR-181a |
| miR-31 | miR-223 |
| miR-31 | miR-424 |
| miR-34a | miR-92a-1 |
| miR-34a | miR-106a |
| miR-34a | miR-125a |
| miR-34a | miR-126 |
| miR-34a | miR-125b |
| miR-34a | miR-142-3p |
| miR-34a | miR-146a |
| miR-34a | miR-150 |
| miR-34a | miR-155 |
| miR-34a | miR-181a |
| miR-34a | miR-223 |
| miR-34a | miR-424 |
| miR-92a-1 | miR-106a |
| miR-92a-1 | miR-125a |
| miR-92a-1 | miR-126 |
| miR-92a-1 | miR-125b |
| miR-92a-1 | miR-142-3p |
| miR-92a-1 | miR-146a |
| miR-92a-1 | miR-150 |
| miR-92a-1 | miR-155 |
| miR-92a-1 | miR-181a |
| miR-92a-1 | miR-223 |
| miR-92a-1 | miR-424 |
| miR-106a | miR-125a |
| miR-106a | miR-126 |

TABLE 3-continued miRNA Binding Site Pairs

| Binding Site 1 | Binding Site 2 |
| --- | --- |
| miR-106a | miR-125b |
| miR-106a | miR-142-3p |
| miR-106a | miR-146a |
| miR-106a | miR-150 |
| miR-106a | miR-155 |
| miR-106a | miR-181a |
| miR-106a | miR-223 |
| miR-106a | miR-424 |
| miR-125a | miR-126 |
| miR-125a | miR-125b |
| miR-125a | miR-142-3p |
| miR-125a | miR-146a |
| miR-125a | miR-150 |
| miR-125a | miR-155 |
| miR-125a | miR-181a |
| miR-125a | miR-223 |
| miR-125a | miR-424 |
| miR-126 | miR-125b |
| miR-126 | miR-142-3p |
| miR-126 | miR-146a |
| miR-126 | miR-150 |
| miR-126 | miR-155 |
| miR-126 | miR-181a |
| miR-126 | miR-223 |
| miR-126 | miR-424 |
| miR-125b | miR-142-3p |
| miR-125b | miR-146a |
| miR-125b | miR-150 |
| miR-125b | miR-155 |
| miR-125b | miR-181a |
| miR-125b | miR-223 |
| miR-125b | miR-424 |
| miR-142-3p | miR-146a |
| miR-142-3p | miR-150 |
| miR-142-3p | miR-155 |
| miR-142-3p | miR-181a |
| miR-142-3p | miR-223 |
| miR-142-3p | miR-424 |
| miR-146a | miR-150 |
| miR-146a | miR-155 |
| miR-146a | miR-181a |
| miR-146a | miR-223 |
| miR-146a | miR-424 |
| miR-150 | miR-155 |
| miR-150 | miR-181a |
| miR-150 | miR-223 |
| miR-150 | miR-424 |
| miR-155 | miR-181a |
| miR-155 | miR-223 |
| miR-155 | miR-424 |
| miR-181a | miR-223 |
| miR-181a | miR-424 |
| miR-223 | miR-424 |

Example 4: In Vivo Studies

Figure 8:
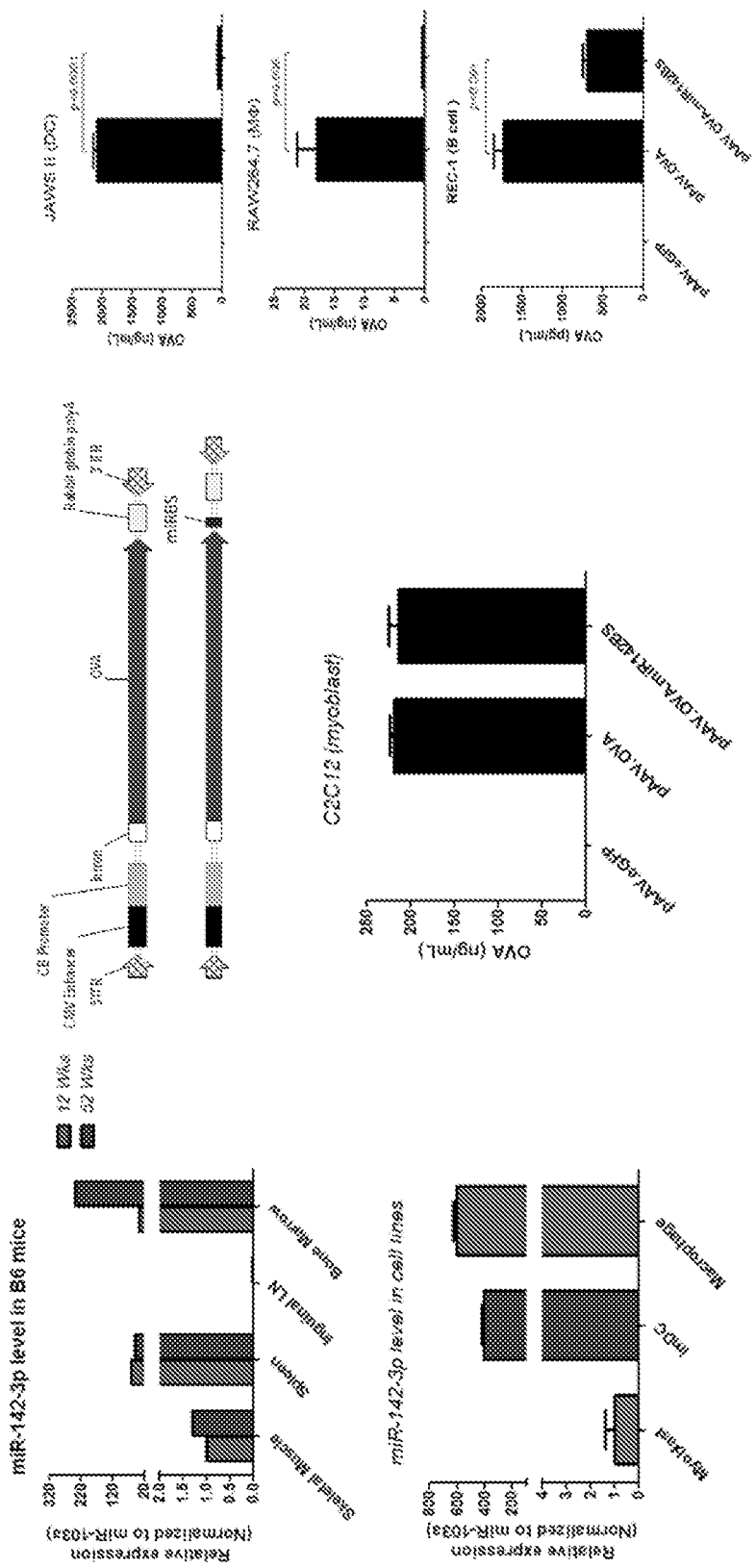
FIG. 8 shows that incorporating miR-142-3p binding sites inhibits transgene expression in antigen presenting cells, but not in muscle cells.

FIG. 8 provides data indicating that incorporating miR-142-3p binding sites inhibits transgene expression in antigen presenting cells, but not in muscle cells.

Figure 9:
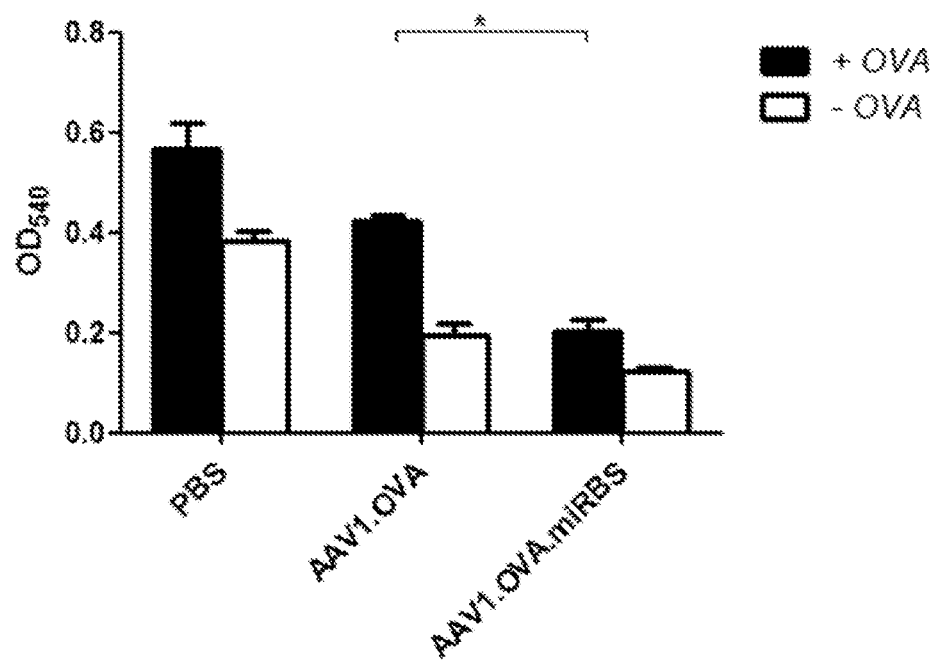
FIG. 9 shows reduced lymphocyte proliferation in mice treated with miRNA-regulated rAAV.OVA.

A lymphocyte proliferation assay was also performed. Six-week-old C57BL/6 female mice were injected (i.m.) with PBS, AAV1.CB6.PI.OVA or AAV1.CB6.PI.OVA.miR (142+155)BS2x (1e11 GC/mouse). 21 weeks after injection, splenocytes were isolated and cultured with and without OVA for 72 hours. Cells were centrifuged and resuspended in fresh media and incubated with MTT for 4 hours. $OD_{540}$ was then determined. Results, shown in FIG. 9, indicate reduced lymphocyte proliferation in mice treated with miRNA-regulated rAAV.OVA compared to control mice.

Figure 10:
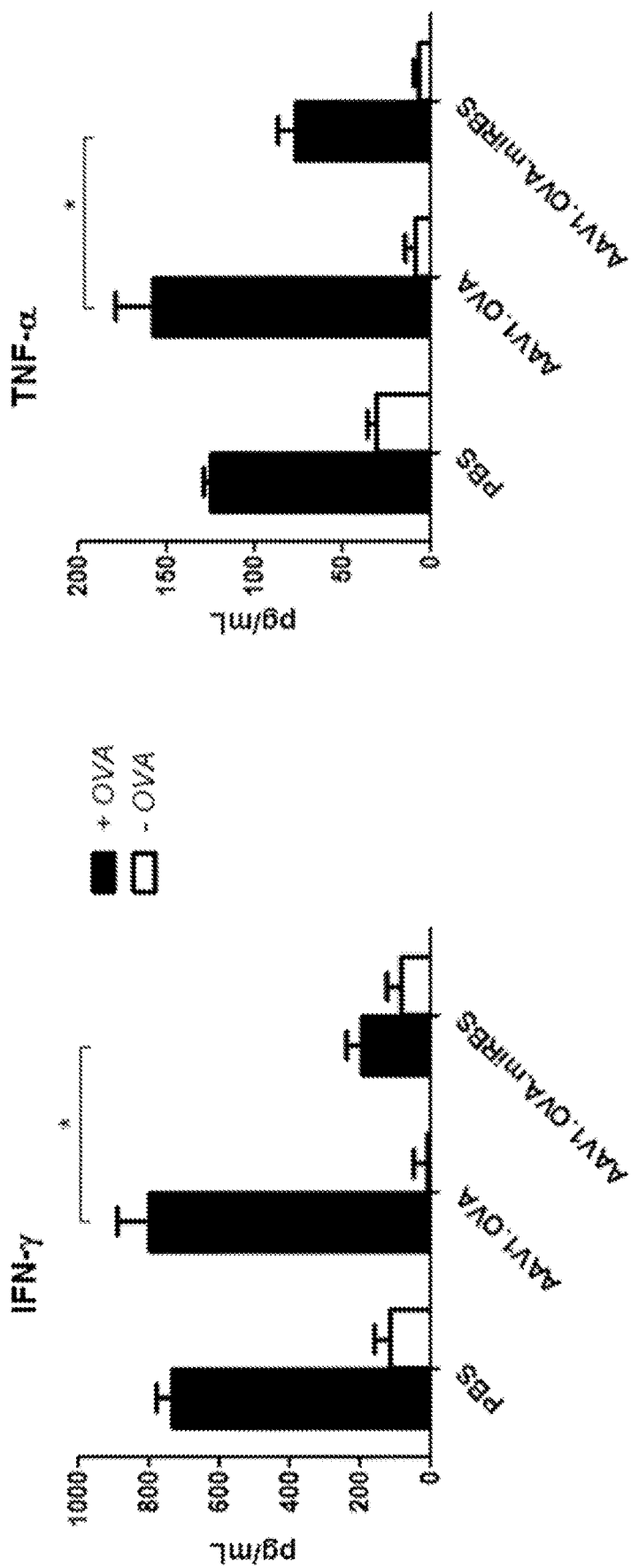
FIG. 10 shows reduced IFN-γ and TNF-α in mice treated with miRNA-regulated rAAV.OVA.

Levels of IFN-γ and TNF-α were also measured in vivo. Six-week-old C57BL/6 female mice were injected (i.m.) with PBS, AAV1.CB6.PI.OVA or AAV1.CB6.PI.OVA.miR (142+155)BS2x (1e11 GC/mouse). 21 weeks after injection, splenocytes were isolated and cultured with and without OVA for 72 hours. Supernatants were collected for cytokine analysis. Results, shown in FIG. 10, indicate reduced IFN-γ and TNF-α in mice treated with miRNA-regulated rAAV.OVA compared to control mice.

Figure 11:
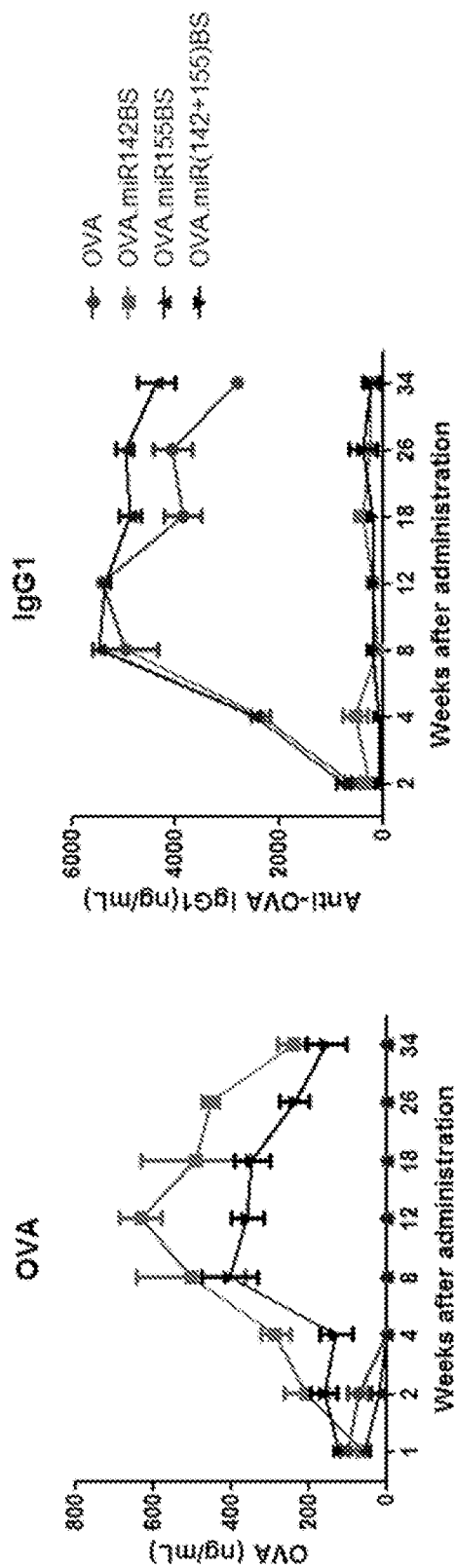
FIG. 11 shows incorporating miR142 binding sites sustained OVA expression with negligible IgG1 level in vivo.

The relationship of transgene expression levels and host immune response was also studied. Six-week-old male C57BL/6 mice were injected (i.m.) with PBS or indicated AAV1 vectors (1e11 GC/mouse, n=9-10/group). Sera were collected weekly for OVA (ELISA) analysis. FIG. 11 shows that incorporating miR142 Binding sites sustained OVA expression with negligible IgG1 level in vivo.

Figure 12:
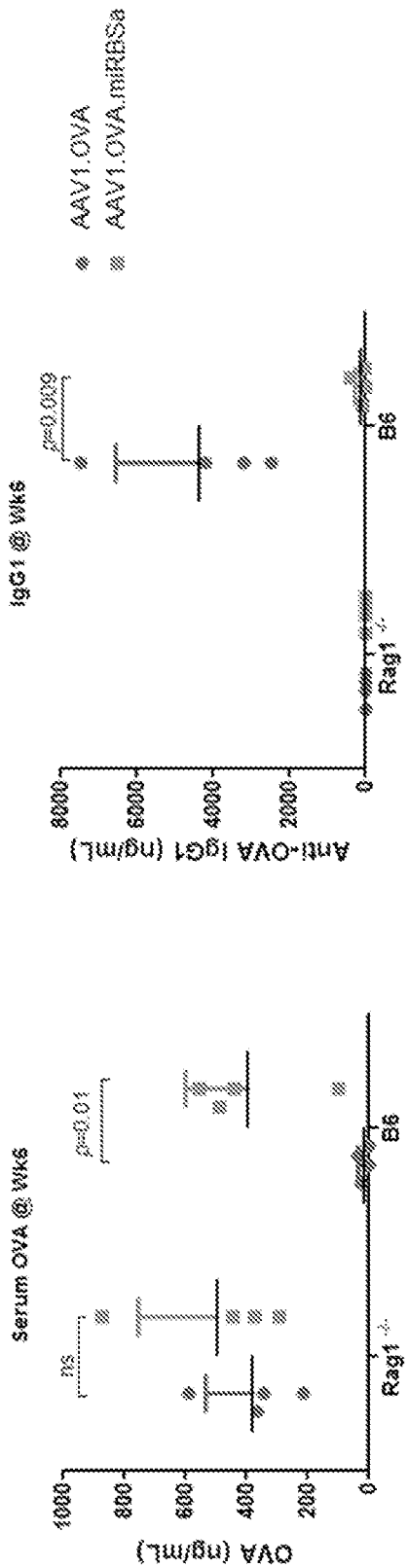
FIG. 12 shows miRNA binding sites-based regulation of transgene expression counteracts host adaptive immunity.

Four-week-old male RAG-1 (Recombination Activation Gene) deficient mice or C57BL/6 mice were injected (i.m.) with PBS or indicated AAV1 vectors (1e11 GC/mouse, n=4/group). Sera were collected weekly for OVA (ELISA) analysis. Results, shown in FIG. 12, indicate that miRNA binding sites-based regulation of transgene expression counteracts host adaptive immunity.

Figure 13:
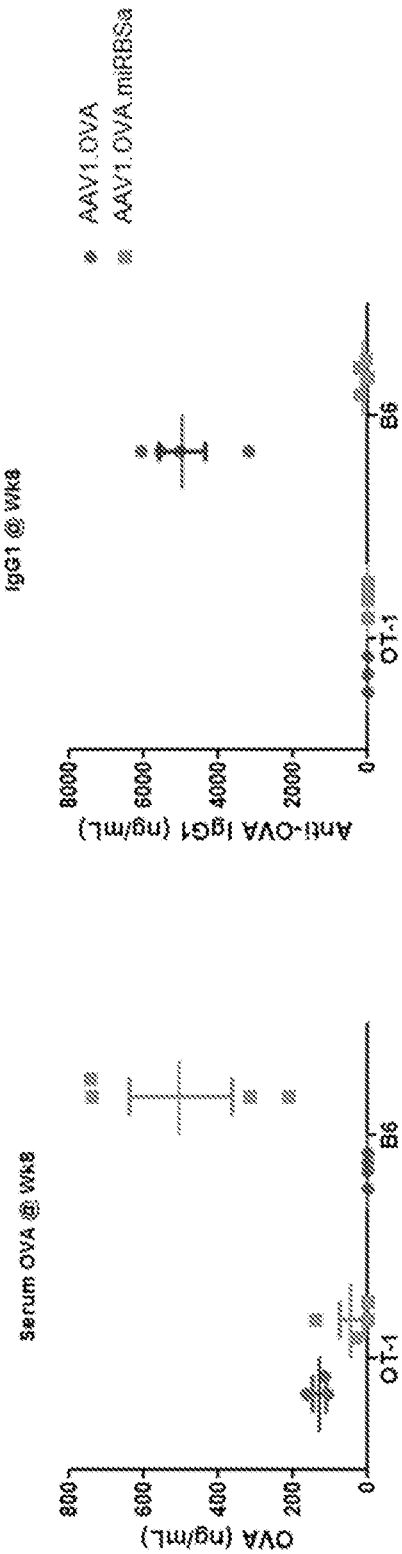
FIG. 13 shows CD8+ T cell response contributes to the loss of AAV-mediated transgene expression.

Four-week-old male OT-1 (OT-1 specific TCR Tg mice) or C57BL/6 mice were injected (i.m.) with PBS or indicated AAV1 vectors (1e11 GC/mouse, n=3-4/group). Sera were collected weekly for OVA (ELISA) analysis. Results, shown in FIG. 13 indicate that CD8+ T cell response contributes the loss of AAV-mediated transgene expression.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method of delivering a transgene to target cells of a subject, the method comprising intramuscularly administering to the subject a recombinant Adeno-Associated Virus (rAAV) comprising the transgene,
    wherein the transgene comprises a promoter operably linked to a nucleic acid sequence that encodes an RNA transcript that comprises two different immune-associated miRNA binding sites, wherein the two different immune-associated miRNA binding sites comprise an miRNA pair selected from: (i) miR-142-3p and miR-155, (ii) miR-146a and miR-150, (iii) miR-424 and miR-150, (iv) miR-181a and miR-21, (v) miR-16-1 and miR-150, (vi) miR-146 and miR-181a, (vii) miR-31 and miR-181a, (viii) miR-146a and miR-16-1, (ix) miR-150 and miR-181a, (x) miR-16-1 and miR-181a, and (xi) miR-142-3p and miR-223;
    wherein the rAAV infects the target cells of the subject,
    wherein the target cells are muscle cells, and
    wherein, following the administration, the transgene is expressed in the muscle cells at a higher level than in antigen presenting cells of the subject.

2. The method of claim 1, wherein the antigen presenting cells are dendritic cells, macrophages, T-lymphocytes, or B-lymphocytes.

3. The method of claim 1, wherein the RNA transcript encodes a therapeutic protein.

4. The method of claim 3, wherein the therapeutic protein comprises between 2 and 20 Glycine-Alanine repeats at a terminal end of the protein.

5. The method of claim 3, wherein the therapeutic protein is selected from the group consisting of: an aromatic L-amino acid decarboxylase (AADC), a frataxin, a SOD1, an insulin, a Human Factor IX, a tumour necrosis factor (TNF)-specific antibody, a human epidermal growth factor receptor 2, a (HER2)-specific antibody, a vascular endothelial growth factor A (VEGF A)-specific antibody, a CD20-specific antibody, a SIV-specific antibody, a TNF-α-specific antibody, a HER1-specific antibody, a CTLA-4-specific antibody, a BAFF-specific antibody, a HIV-specific antibody, a CD11a-specific antibody, a CD25-specific antibody, a CD30-specific antibody, a CD33-specific antibody, and a CD52-specific antibody.

6. The method of claim 3, wherein the therapeutic protein comprises an antigen-binding protein, an antigen-binding protein fragment, an immunoglobulin heavy chain, or a light chain.

7. The method of claim 1, wherein the rAAV comprises a capsid of a serotype selected from: an AAV1, an AAV2, an AAV3, an AAV4, an AAV5, an AAV6, an AAV7, an AAV8, an AAV9, an AAV10, an AAV11, and an AAV12.

\* \* \* \* \*

SEQUENCE LISTING

```
<160> NUMBER OF SEQ ID NOS: 26

<210> SEQ ID NO 1
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 1
cacaaaccat tatgtgctgc ta                                              22

<210> SEQ ID NO 2
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 2
cgccaatatt tacgtgctgc ta                                              22

<210> SEQ ID NO 3
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 3
ctaccagcac tgtaagcact ttg                                             23
```

```
<210> SEQ ID NO 4
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 4
ctatctgcac tagatgcacc tta                                              23

<210> SEQ ID NO 5
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 5
tcagttttgc atagatttgc aca                                              23

<210> SEQ ID NO 6
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 6
ctacctgcac tataagcact tta                                              23

<210> SEQ ID NO 7
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 7
gctggatgca aacctgcaaa act                                              23

<210> SEQ ID NO 8
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 8
tcaacatcag tctgataagc ta                                               22

<210> SEQ ID NO 9
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 9
taaccgattt cagatggtgc ta                                               22

<210> SEQ ID NO 10
<211> LENGTH: 23
<212> TYPE: DNA
<213> ORGANISM: Artificial Sequence
<220> FEATURE:
<223> OTHER INFORMATION: Synthetic polynucleotide
```

```
<400> SEQUENCE: 10
aacactgatt tcaaatggtg cta                                           23

<210> SEQ ID NO 11
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 11
taaccgattt caaatggtgc ta                                            22

<210> SEQ ID NO 12
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 12
agctgagtgt aggatgttta ca                                            22

<210> SEQ ID NO 13
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 13
cagctatgcc agcatcttgc ct                                            22

<210> SEQ ID NO 14
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 14
acaaccagct aagacactgc ca                                            22

<210> SEQ ID NO 15
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 15
agcattgcaa ccgatcccaa cct                                           23

<210> SEQ ID NO 16
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 16
ctacctgcac tgtaagcact ttt                                           23

<210> SEQ ID NO 17
```

```
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 17
tcacaggtta aagggtctca ggga                                              24

<210> SEQ ID NO 18
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 18
cgcattatta ctcacggtac ga                                                22

<210> SEQ ID NO 19
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 19
tcacaagtta gggtctcagg ga                                                22

<210> SEQ ID NO 20
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 20
tccataaagt aggaaacact aca                                               23

<210> SEQ ID NO 21
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 21
aacccatgga attcagttct ca                                                22

<210> SEQ ID NO 22
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 22
cactggtaca agggttggga ga                                                22

<210> SEQ ID NO 23
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 23
```

```
accccctatca caattagcat taa                                              23

<210> SEQ ID NO 24
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 24
actcaccgac agcgttgaat gtt                                               23

<210> SEQ ID NO 25
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 25
tggggtattt gacaaactga ca                                                22

<210> SEQ ID NO 26
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 26
ttcaaaacat gaattgctgc tg                                                22
```